(12) United States Patent
Cowman et al.

(10) Patent No.: US 10,723,812 B2
(45) Date of Patent: Jul. 28, 2020

(54) METHOD FOR SEPARATING HYALURONAN AND QUANTIFYING ITS MOLECULAR MASS DISTRIBUTION IN BIOLOGICAL SAMPLES

(71) Applicant: NEW YORK UNIVERSITY, New York, NY (US)

(72) Inventors: Mary Cowman, Mohegan Lake, NY (US); Han Yuan, New York, NY (US); Ripal Amin, Gujarat (IN)

(73) Assignee: NEW YORK UNIVERSITY, New York, NY (US)

( * ) Notice: Subject to any disclaimer, the term of this patent is extended or adjusted under 35 U.S.C. 154(b) by 486 days.

(21) Appl. No.: 15/116,393

(22) PCT Filed: Feb. 6, 2015

(86) PCT No.: PCT/US2015/014742
§ 371 (c)(1),
(2) Date: Aug. 3, 2016

(87) PCT Pub. No.: WO2015/120223
PCT Pub. Date: Aug. 13, 2015

(65) Prior Publication Data
US 2016/0347869 A1    Dec. 1, 2016

Related U.S. Application Data

(60) Provisional application No. 62/100,654, filed on Jan. 7, 2015, provisional application No. 61/936,503, filed on Feb. 6, 2014.

(51) Int. Cl.
| | | |
|---|---|---|
| *G01N 31/00* | (2006.01) | |
| *G01N 33/53* | (2006.01) | |
| *C08B 37/08* | (2006.01) | |
| *G01N 33/66* | (2006.01) | |

(52) U.S. Cl.
CPC ..... *C08B 37/0072* (2013.01); *G01N 33/5308* (2013.01); *G01N 33/66* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 5,559,104 A | 9/1996 | Romeo | |
| 7,507,723 B2* | 3/2009 | Asari | A61K 31/702 |
| | | | 514/54 |
| 2005/0090661 A1* | 4/2005 | Asari | A61K 31/702 |
| | | | 536/53 |
| 2007/0117188 A1 | 5/2007 | DeAngelis | |
| 2008/0152640 A1 | 6/2008 | Prehm | |

* cited by examiner

*Primary Examiner* — Lisa V Cook
(74) *Attorney, Agent, or Firm* — Browdy and Neimark, PLLC

(57) ABSTRACT

The present invention provides a facile method for separation (fractionation) of HA in a sample over a broad M range, including low M HA, by ion exchange (IEX) chromatography. The present invention also provides an assay method for quantifying in a sample the presence of low M HA in total HA isolated from a biological source. The method involves HA fractionation according to M by use of IEX separation, followed by HA-specific assay of HA size range fractions.

17 Claims, 12 Drawing Sheets

METHOD FOR SEPARATING HYALURONAN AND QUANTIFYING ITS MOLECULAR MASS DISTRIBUTION IN BIOLOGICAL SAMPLES

GOVERNMENT LICENSE RIGHTS

This invention was made with government support under grant number R01 HD061918 awarded by the National Institutes of Health. The government has certain rights in the invention.

BACKGROUND OF THE INVENTION

Field of the Invention

The present invention relates to a method for size-dependent fractionation and determination of molecular mass (M) distribution of hyaluronan (HA) in biological samples.

Description of the Related Art

Hyaluronan (HA) is a polymeric extracellular glycosaminoglycan composed of repeating units of disaccharides of β-D-glucuronic acid and N-acetyl-β-D-glucosamine. HA is nearly ubiquitous in vertebrate solid and liquid tissues. It is a key macromolecular component of eye vitreous, articular joint synovial fluid, cartilage, and skin. HA is normally synthesized as a high molecular mass (M) polymer, generally ranging from about 1000-8000 kDa. HA synthase enzymes are integral membrane proteins of the cell surface, which synthesize HA as a pure polysaccharide polymer and extrude it into the extracellular matrix. HA chains can be released from the cell surface, or can be maintained as part of a pericellular layer, via noncovalent attachment to cell surface receptor proteins such as CD44. HA serves to organize proteoglycans of the pericellular and extracellular matrices via noncovalent binding interactions with their protein cores. It also controls the equilibrium partition and translational diffusion of other macromolecules near the cell surface via macromolecular crowding, and further maintains hydration of the pericellular matrix via osmotic pressure effects. In all of these properties, high M of HA is a critical requirement.

Assay of HA concentration in biological fluids such as blood serum has been shown to be useful in diagnosis of liver disease, because HA is normally rapidly removed from the blood by healthy liver. HA concentration in synovial fluid is reduced as fluid volume increases in osteoarthritis and rheumatoid arthritis, despite increased synthesis. The HA content of many solid tissues has been shown to increase in the presence of inflammation. Many disease states are accompanied by inflammation, and also have elevated HA levels. For example, lung carcinoma has greatly elevated levels of HA relative to normal lung tissue.

Reduction in the average M of HA in biological tissues and fluids is associated with inflammatory processes. Increased expression or activity of endogenous hyaluronidases can reduce the chain length of HA, and has been documented in various disease states. In addition, reactive oxygen and nitrogen species (ROS/RNS) are generated in inflammatory processes, and these can degrade HA by chemical means. Thus, low M HA can be generated by degradative processes, including those dependent on reactive oxygen and nitrogen species (ROS/RNS) and also by action of hyaluronidase enzymes. There are many different possible low M HA species, and the biological activity is believed to be dependent on the average M and polydispersity in M.

There is usually compensatory increase in HA synthesis, but the relative rates of HA synthesis and HA fragmentation determine the overall M distribution. When degradation exceeds synthesis, low M HA might exist in significant amounts.

Low M HA is a cell-signaling biomolecular species in biological tissues and fluids, believed to be a natural danger signal. Low M HA can be a natural stimulant for host defense against insults such as microbial attack. Response to low M HA is tissue-specific and dependent on the physiological state. Low M HA can regulate cell activity by interacting with receptor proteins, which causes signaling of a number of responses in an M-dependent manner, such as its signaling through cell surface receptors like CD44 and TLR2/4, as well as soluble HA receptors such as RHAMM. Clustering of cell surface CD44 when bound to polymeric high M HA is eliminated when bound to short HA fragments. This can lead to induction of cytokine and chemokine gene expression in macrophages, or cell death in activated T cells. The receptors CD44 and RHAMM bind low M HA in a manner leading to specific signaling processes. These include stimulation of NFκB signaling pathways and expression of pro-inflammatory cytokines and chemokines. Low M HA is believed to act as an endogenous danger signal, activating Toll-like receptors TLR2 and TLR4, and inducing changes in gene expression for mediators of host defense against microbes, mediators of inflammation response, and proteins connected with cell migration. HA signaling via TLR2/4 is speculated to occur by direct binding but this has not yet been proven.

The probable association of inflammation with the presence of low M HA indicates a need for improved and highly sensitive methods to accurately analyze the full M distribution of HA in biological tissues and fluids, including the fraction of low M.

The average M and distribution of M for HA present in biological sources has been studied primarily for fluid tissues such as synovial fluid, vitreous, serum, and lymph (Laurent and Granath, 1983; Dahl et al., 1985, 1986; Tengblad et al., 1986; Lee and Cowman, 1994; Armstrong and Bell, 2002). To date, the content of very low M HA (less than about 100 kDa) has been unidentified. Since low M HA is difficult to purify, specific detection of the separated HA is necessary. Because the low M HA is a signaling species, its content is also expected to be low and will require highly sensitive detection. Sandwich assays have proven incapable of detecting HA with M less than about 20 kDa, and have a severe M dependence of detection for HA between about 20 and 150 kDa (Yuan et al., 2013). Similarly, HA detection after blotting to membrane surfaces (used for the electrophoretic methods) has proven incapable of properly detecting HA with M less than about 150 kDa.

Most current methods for determination of the M distribution of HA from tissues and biological fluids have been optimized for high M HA (greater than about 200 kDa). Commonly employed methods are size exclusion chromatography with multiangle laser light scattering (SEC-MALLS), and agarose or polyacrylamide gel electrophoresis (Min et al., 1986; Kvam et al., 1993; Lee et al., 1994; Adam et al., 2001; Baggenstoss et al., 2006; Cowman et al., 2011; and Bhilocha et al., 2011). Detection of very low M HA by light scattering is inherently insensitive, and the SEC-MALLS method requires a highly purified HA sample. Gel electrophoresis can analyze samples on the microgram scale, and can tolerate some impurities in the sample, but nonspecific staining by those impurities can interfere with size distribution analysis of the HA. Blotting of gels to positively charged nylon and detection of HA using a labeled specific binding protein (Lee et al., 1994) works only for HA with M greater than about 100 kDa, as a result of strong surface binding (Yuan et al., 2013). Most alternative methods have similar limitations. Capillary electrophoresis (CE) (Hayase et al., 1997) is limited to pure HA samples. MALDI-TOF mass spectrometry (Mahoney et al., 2001 and Volpi et al., 2007) has high sensitivity, but requires a pure sample and HA with M larger than about 10 kDa becomes difficult to analyze (Yeung et al., 1999). The most promising method to date for complete size distribution analysis of HA isolated from biological samples is size exclusion chromatography-enzyme linked sorbent assay (SEC-ELSA) (Laurent et al., 1983; Tengblad et al., 1986; and Sasaki et al., 2011), because it is both sensitive and specific. However, SEC-ELSA has never been applied to the analysis of HA with M lower than about 100 kDa. A new method that has extremely high sensitivity and works best for low M HA is GEMMA (gas-phase electrophoretic mobility molecular analysis), but its accuracy has not yet been established for impure and polydisperse HA samples (Malm et al., 2012).

Anion exchange chromatography has not previously been applied to the determination of the M distribution for HA as isolated from biological sources, where there is a broad size distribution. Anion exchange chromatography with gradient elution using salt solutions of increasing ionic strength has been used previously only to separate short oligosaccharide fragments of HA by degree of polymerization and thus total charge (since there is one negative charge per disaccharide repeat unit). Success has been limited to fragments containing from 1 to about 20 disaccharides (0.4-8 kDa) (Weissmann, Meyer et al. 1954, Nebinger 1985, Holmbeck and Lerner 1993, Mahoney et al. 2001, Tawada et al. 2002). Short fragments of sulfated glycosaminoglycans, their desulfated products, or hybrid oligosaccharides created by transglycosylation have also been separated by anion exchange chromatography. Fragments containing 1 to approximately 20 disaccharides (ca. 10 kDa) were separated by size using an elution gradient of increasing ionic strength (Hoffman et al. 1956, Yamashina et al. 1963, Inoue and Nagasawa 1981, Lauder et al. 2000). No glycosaminoglycans have previously been fractionated by size/degree of polymerization/total charge for sizes above about 8-10 kDa. It has generally been expected that fragments larger than about 10 kDa would not be fractionated on the basis of size using ion exchange methods, due to small differences in total charge between long chains.

DNA and RNA oligonucleotides have been separated according to degree of polymerization over a much larger size range (Kato et al. 1983, Kato et al. 1988, Kato et al. 1989, Strege and Lagu 1991, Baba et al. 1993). DNA restriction fragments containing up to about 600 base pairs (ca. 390 kDa) could be separated into distinct peaks if fragment sizes differed by at least 5-10%. Further size-dependence of separation with low resolution could be achieved up to about 23,000 base pairs (ca. 15 MDa). The separation of high M DNA fragments used nonporous anion exchange media, because the large hydrodynamic volume of DNA molecules in solution makes entry into porous media difficult. Porous media may overlay a gel filtration separation mode on the ion exchange mode.

There is currently no facile method that has been shown to provide fractionation and specific quantification of HA over a broad M range including both low and high M.

Human milk provides newborns with a critical first line of natural defense against harmful infectious agents in addition to providing essential nutrition and factors that promote growth as well as organ and immune system development. Multiple components of milk, including carbohydrates, proteins, and fatty acids, work in concert to achieve protection against intestinal pathogens and formation of a beneficial microbiota that is essential to the future health of the baby (Newburg et al., 2005 and Ballard et al., 2013). Human milk oligosaccharides (HMOs) have been appreciated as beneficial glycans that promote healthy commensal bacteria and pathogen protection within the infant gut for over sixty years (Bode 2012). Similarly milk glycosaminoglycans have been shown to play a protective role, by inhibiting HIV infection (Newburg et al., 1995). Coppa et al., 2011 recently reported that hyaluronan (HA), a nonsulfated glycosaminoglycan extracellular matrix component produced by all vertebrates, is a natural component of human milk.

There are several challenges associated with the characterization of HA from human milk. Milk is a highly complex fluid, and standard HA isolation procedures are insufficient for removal of all contaminants. Even proteinase K cannot digest all of the protein components of milk. Initial efforts to analyze the molecular mass distribution of isolated milk HA by gel electrophoresis were unsuccessful, due to substantial staining interference by known (e.g., chondroitin or sulfated glycosaminoglycans) and unknown contaminants. The concentration of HA in milk is also very low, so that methods of high sensitivity are required for analysis of the isolated HA.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a facile method for separation (fractionation) of HA in a sample over a broad M range, including low M HA, by ion exchange (IEX) chromatography. Any size fraction of low M HA can be isolated using this separation/fractionation method.

The present invention also provides an assay method for quantifying in a sample the presence of low M HA in total HA isolated from a biological source. The method involves HA fractionation according to M by use of IEX separation, followed by HA-specific assay of HA size range fractions.

BRIEF DESCRIPTION OF THE DRAWINGS

(FIG. 2A) Fractions on a 4-20% gradient polyacrylamide gel stained with STAINS-ALL dye (3,3'-dimethyl-9-methyl-4,5,4',5'-dibenzothiacarbocyanine). Lane 1: untreated polydisperse HA, 4 µg. Lane 2: mixture of equal portions of the isolated IEX fractions ("recombine"), 4 µg if no loss occurred. Lane 3: Loladder containing HA molecular mass markers 495, 310, 214, 110, and 30 kDa, in addition to purified 7.6-10 kDa HA. Lanes 4-10: HA eluted with 0.800, 0.440, 0.416, 0.400, 0.360, 0.330 and 0.300 M NaCl solutions, respectively. The electrophoretic separation was performed as described by the Bhilocha et al. (2011) modification of the Min and Cowman (1986) polyacrylamide gel electrophoresis method. (FIG. 2B) Densitometric analysis of HA fractions obtained by IEX. Scans correspond to sample lanes 4-10 of the gel in FIG. 2A. Migration distance is scaled to M by comparison with co-electrophoresed HA standards. Each IEX fraction has low polydispersity, in contrast to the overall high polydispersity of the additive sum of the sample fractions. The average M and range of M (width at half height) for each fraction is obtained from these profiles as described by Cowman et al. (2011) and Bhilocha et al. (2011). (FIG. 2C) Densitometric scans of sample lanes 1 and 2 from the stained 4-20% polyacrylamide gel of FIG. 2A, with migration distance scaled to M by comparison with co-electrophoresed standards. The profile of the original mixture is highly similar to that of the recombined IEX fractions, and to the additive sum of the individual fraction profiles. The result indicates IEX fractionation of HA causes no overall or size-preferential losses, and maintains the true original M distribution.

(FIG. 9A) 3% agarose gel. Lane 1: untreated polydisperse HA, 4 µg. Lane 2: mixture of equal portions of the isolated IEX fractions ("recombine"), 4 µg if no loss occurred. Lane 3: Loladder containing HA molecular mass markers 495, 310, 214, 110, and 30 kDa, in addition to purified 7.6-10 kDa HA. Lanes 4-10: HA eluted with 0.800, 0.440, 0.416, 0.400, 0.360, 0.330 and 0.300 M NaCl solutions, respectively. (FIG. 9B) Densitometric analysis of HA fractions obtained by IEX. Scans correspond to sample lanes 4-10 of the gel. Migration distance is scaled to M by comparison with co-electrophoresed HA standards. Each IEX fraction has low polydispersity, in contrast to the overall high polydispersity of the additive sum of the sample fractions. The agarose gel separates fractions with higher M better than the polyacrylamide gel. (FIG. 9C) Densitometric scans of sample lanes 1 and 2 from the stained 3% agarose gel. The profile of the original mixture is highly similar to that of the recombined IEX fractions, and to the additive sum of the individual fraction profiles. The result indicates IEX fractionation of HA causes no overall or size-preferential losses, and maintains the true M distribution.

(FIG. 10A) 4-20% polyacrylamide gel electrophoresis of fractions of a polydisperse HA sample obtained by 4 elution steps from an IEX spin column using NaCl solutions of increasing concentration. Lane 1: untreated polydisperse HA, 4 µg. Lane 2: mixture of equal portions of the isolated IEX fractions ("recombine"), 4 µg if no loss occurred. Lane 3: Loladder containing HA molecular mass markers 495, 310, 214, 110, and 30 kDa, in addition to purified 7.6-10 kDa HA. Lanes 4-7: HA eluted with 0.800, 0.460, 0.425, 0.360 M NaCl solutions, respectively. (FIG. 10B) Densitometric scans of sample lanes 1 and 2 from the stained 4-20% polyacrylamide gel of FIG. 9A are illustrated with migration distance scaled to M by comparison with co-electrophoresed standards. The profile of the original mixture is highly similar to that of the recombined IEX fractions and to the additive sum of the individual fraction profiles.

DETAILED DESCRIPTION OF THE INVENTION

Figure 1:
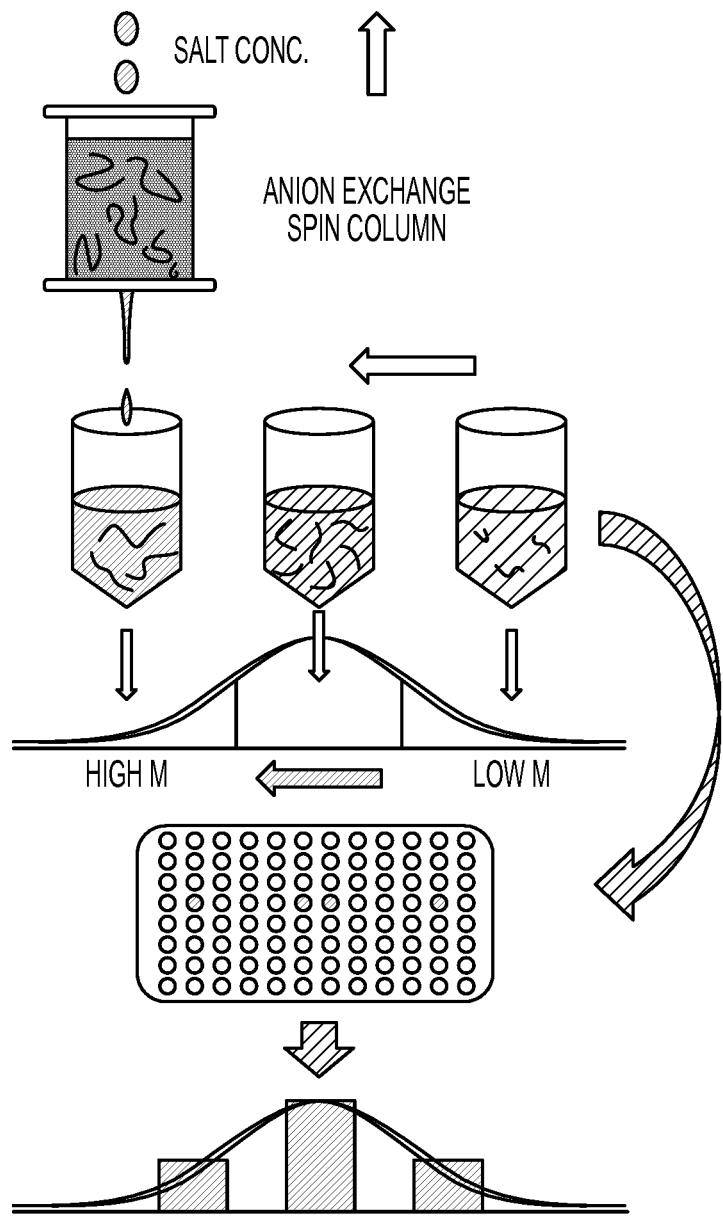
FIG. 1 shows a scheme for determination of HA molecular mass distribution by ion exchange fractionation and specific HA quantification. HA was fractionated according to molecular mass using stepwise elution from an ion exchange column with solutions of increasing salt concentration. HA in each fraction was quantified by competitive Enzyme Linked Sorbent Assay (ELSA).

The present invention provides a method for separating (fractionating) HA on the basis of size (molecular mass M). Ion exchange (IEX) fractionation is employed for this method. The ion exchange separation can be accomplished by rapid step or gradient elution processes. It can utilize any appropriate support medium with immobilized cationic functional groups capable of binding HA, allowing dissociation/elution with various ionic agents to reduce the affinity of HA for the support. The present invention represents an improvement over existing methods for separation of HA on the basis of M, because it employs IEX chromatographic separation rather than size exclusion chromatography. This simultaneously allows removal of sulfated glycosaminoglycans, which have higher charge density and require higher salt to elute, and also provides sub-fractionation of HA according to degree of polymerization/total charge/molecular mass.

The present method for separating HA on the basis of molecular mass (M) involves applying a sample of HA, such as from a biological source, to an anion exchange matrix, and then eluting the HA in the sample with salt solutions or a salt solution gradient of increasing concentration into a plurality of fractions to separate HA by size, where the HA present in the sample in a size range between about 10 to 150 kDa are separated into at least three different size range fractions. Preferably, the size range of HA separated into at least three different size range fractions is from 10 to 80 kDa. HA in either of the above two size ranges is preferably separated into 3, 4, 5, 6, 7, or 8 fractions. Additional fractions for HA above or below the 10 to 150 kDa size range may also be obtained in this method. Preferably, HA greater than about 80 kDa, greater than about 100 kDa, or greater than about 110 kDa are separated in at least one size fraction. For example, when the HA in a sample is separated into at least three different size range fractions, at least two of these size range fractions are in the size range of about 10 to about 80 or to about 100 kDa, and preferably with at least one other size fraction being a high M HA size fraction greater than about 80 kDa or greater than about 100 kDa. As another non-limiting example, when the HA in a sample is separated into at least four different size range fractions, then at least three of size range fractions are in the size range of about 10 to about 110 kDa, and preferably with at least one other size fraction being a high M size fraction greater than about 80 kDa. The specific size range in each size range fraction separated/fractionated by the present method can be determined by correlation of HA size reference standards with salt concentration for elution from the anion exchange matrix.

The anion exchange step to fractionate HA may employ any of numerous suitable resins or supporting matrices and attached functional groups well known in the art. For example, the matrix may be a porous material based on regenerated cellulose, agarose, dextran, or other polymers or combinations of polymers. Alternatively, available nonporous matrices of a material such as polystyrene/divinyl benzene in the form of beads may be used. The functional groups attached to the matrices are usually strong anion exchangers, such as quaternary ammonium groups, or alternatively may be weak anion exchangers, such as those containing diethylaminoethyl or diethylaminopropyl groups. A variety of suitable anion exchangers are well known in the art.

The anion exchange fractionation may be accomplished using spin columns or multi-well filter plates containing the ion exchange matrices. In these formats, stepwise elution is effected using salt solutions of increasing concentration, driven through the matrix by centrifugation or vacuum filtration. Other formats suitable for the fractionation are chromatographic columns using, for example, pump-driven stepwise elution or gradient elution of salt solutions.

The salt solution for eluting HA may be a simple salt such as sodium chloride, but other cations, such as lithium and ammonium, and other anions, such as acetate, phosphate, bicarbonate, sulfate and perchlorate, may also be used, as would be well recognized in the art.

In an example presented below, a simple anion exchange spin column is employed to isolate HA fractions having known average M, and low polydispersity in M, from crude HA extracted from biological tissues and fluids. This specific example is but one possible type of IEX that may be used for HA fractionation.

The IEX fractionation can be differentially optimized to provide HA fractions of specific average M. In one embodiment, the method can be used to separate high M fractions containing HA greater than about 80 kDa or greater than about 100 kDa from various fractions containing low M HA of desired low polydispersity, in the range of about 10-80 kDa or about 10-100 kDa, respectively.

The present invention also provides for isolating a size fraction from among the different size fractions separated by the present method of separation/fractionation. This may include further purification of the HA in the isolated size fraction using any purification step/stage that is conventional and well recognized in the art of HA.

The present invention further provides an assay method for quantifying in a sample the amount of HA in each of a plurality of size fractions from a size range of about 10 to 150 kDa, preferably about 10 to 80 kDa. This assay method combines the separation of HA on the basis of M, using an IEX step according to the present method for separating HA on the basis of molecular mass (M), with a highly sensitive HA-specific detection step, and can be used to also quantify high M HA in the sample have M greater than about 80 kDa or greater than about 100-110 kDa. The present invention represents an improved assay method over existing gel electrophoretic separation methods for analysis of M distribution of HA, which utilize either nonspecific staining that cannot differentiate HA from other contaminating polyanionic biological molecules, or utilize blotting and specific detection methods that cannot detect HA with M less than 20 kDa, and are severely M-dependent between about 20-150 kDa. The present assay method further provides improved sensitivity in quantifying low M HA obtained from biological sources, where sample size is limiting, relative to existing physicochemical methods (for example, GPC-MALLS: gel permeation chromatography with multi angle laser light scattering) for determination of the M distribution of a polydisperse HA sample.

The specific detection of HA is an important step of the assay method, because purification of low M HA is difficult, and contaminants interfere with nonspecific detection modes. The specificity is based on the use of molecular species such as proteins or proteoglycans that recognize and bind HA but no other biological molecules. For example, the aggrecan proteoglycan binds HA specifically. The intact proteoglycan may be used, or a terminal fragment called G1-IGD-G2 (globular domain 1-interglobular domain-globular domain 2), often referred to as HA binding protein (HABP) or HA binding region (HABR). The Link protein, also called CRTL1 or HAPLN1, is similar to the G1 domain of aggrecan, and is another suitable protein for specific detection of HA. Isolated HABP, usually a mixture of the aggrecan HABR and the Link protein, may also be used. Similarly, the G1 domain of the versican proteoglycan core protein may be used, as well as any HA-binding fragment or portion of the versican or aggrecan proteoglycan. Hyaluronectin, an HA-specific binding protein isolated from brain, is another example of a protein that may be used. The above examples are merely non-limiting examples and not meant to exclude other specific binding molecules. It should be appreciated that a mixture of different HA binding molecules may be used as well.

The type of assay method for determining the amount of HA in each of the plurality of size range fractions as fractionated over an anion exchange matrix is preferably a competitive mode assay. In such assays, including the one employed in the Example presented hereinbelow, HA is usually immobilized on a surface such as the wells of a plastic 96-well plate. Alternative surfaces such as suitably modified magnetic beads may also be used. Soluble HA samples for assay, either standards or unknowns (e.g., size fractionated HA), are mixed with the specific binding agent, usually a protein or proteoglycan. The soluble HA competes with the immobilized surface HA for the specific binding agent, so that the resulting surface-bound amount of the binding agent is a measure of the amount of soluble HA in the sample being analyzed. There are multiple possible detection schemes to quantify the bound agent. For example, if aggrecan proteoglycan is the specific binding agent, it can be quantified with an antibody to the keratan sulfate chains of aggrecan, along with a suitably labeled second antibody. Where the specific binding agent is a labeled (e.g., biotinylated) HABP, it can be quantified by binding of the label to a specific agent such as streptavidin, which is in turn conjugated to an enzyme or other detectable species. Another non-enzyme detection mode uses a fluorescent label for detection and determining the amount of HA. Radiolabeled HABP may also be used but is less desirable on the basis of safety and disposal.

Where low M HA is a small fraction of the total HA present in a tissue or fluid, and the available quantity of HA may be small, the high sensitivity in detection afforded by an enzyme linked immunosorbant (ELISA)-like assay provides the necessary sensitivity. The specificity of the ELISA-like assay further provides the ability to quantify HA in the presence of similar biomolecular species such as chondroitin, which may co-purify with HA.

The specific HA detection method which determines the amount of HA in a sample or in a size fraction may be any method by which HA is detected according to its interaction with specific HA binding peptides, proteins, or other molecular agents, or by which it can be otherwise uniquely identified, as known and recognized in the art. For example, mass spectrometry that detects HA on the basis of size and fragmentation patterns may also be useful. The method should be capable of quantifying HA with little or no dependence on size, or a suitable correction factor can be applied. A preferred embodiment of the assay method uses a competitive ELISA-like assay for HA, such as referred to herein as Enzyme-Linked Sorbent Assay (ELSA).

Having now generally described the invention, the same will be more readily understood through reference to the following example which is provided by way of illustration and are not intended to be limiting of the present invention.

EXAMPLE

To address the issues of limited sample amount, purification difficulty, and the importance of analyzing both high and low M HA simultaneously, a method using size-dependent fractionation of HA by anion exchange on a spin column, and quantification of HA in the fractions using a competitive ELSA assay was developed. HA size analyses were then conducted for samples from 20 different human milk donors to characterize the diversity of HA sizes in milk. Here it is reported that only a small percentage (~5%) falls in the range of the active commercial HA 35 kDa preparation, and the majority has an average molecular mass of ~440 kDa.

Abbreviations Used:

HA, hyaluronan; M, molecular mass; IEX, ion exchange; ELSA, enzyme linked sorbent assay; HBD2, human beta defensin 2; HMOs, human milk oligosaccharides; MuBD3, murine beta defensin 3; TLR4, toll-like receptor 4; SEC-MALLS, size exclusion chromatography with multiangle laser light scattering; CE, capillary electrophoresis; SEC-ELSA, size exclusion chromatography-enzyme linked sorbent assay; GEMMA, gas-phase electrophoretic mobility molecular analysis; STAINS-ALL dye, 3,3'-dimethyl-9-methyl-4,5,4',5'-dibenzothiacarbocyanine; TBE, Tris-borate-EDTA; NaCl, sodium chloride; ERK, Extracellular signal-regulated kinases; MAPK, Mitogen-activated protein kinase; HAS, hyaluronan synthase; bVG1: biotinylated versican G1 domain.

Materials and Methods

Materials

Twenty dated human breast milk samples were provided by 20 unique donors between January 2011 and December 2012. All donors provided informed consent in accordance with a protocol approved by the Cleveland Clinic Institutional Review Board, and provided de-identified samples that were assigned a code number corresponding to postpartum day of milk collection. All samples were stored at −20° C.

Chemoenzymatically synthesized HA standards with narrow size distribution and known average molecular mass determined by size exclusion chromatography with multi-angle light scattering (Select-HA™: specific HA sizes and mixtures of sizes as LoLadder) were obtained from Hyalose LLC (Oklahoma City, Okla., USA). A low M HA sample containing chains 19-25 disaccharides in length (7.6-10.0 kDa) was prepared as previously described (Turner et al., 1988). Polydisperse highly purified HA samples with known average molecular mass (based on measurement of intrinsic viscosity) were purchased from Lifecore Biomedical (Chaska, Minn., USA). Chondroitin 4-sulfate and dermatan sulfate were obtained from Seikagaku Corporation (Tokyo, Japan).

Phosphate-buffered saline (PBS), Tris base, and boric acid were from Sigma Chemical (St. Louis, Mo., USA). Proteinase K was from Roche (Indianapolis, Ind., USA). The hyaluronidase (from *Streptomyces hyaluronolyticus*) was from Seikagaku Corporation (Tokyo, Japan). Sodium chloride (NaCl) was from Fisher Scientific (Waltham, Mass., USA). Stains-All™ dye (3,3'-dimethyl-9-methyl-4,5,4',5'-dibenzothiacarbocyanine) and bromophenol blue tracking dye were obtained from Bio-Rad Laboratories (Hercules, Calif., USA). Polyacrylamide (4-20% gradient) gels in Tris-borate-EDTA (TBE) and streptavidin-coated magnetic beads (M-280) were from Life Technologies (Carlsbad, Calif., USA). Agarose was from GE Healthcare (agarose NA, $-mr=0.10$) (Pittsburgh, Pa., USA). The HA competitive ELISA (ELSA) kit (K-1200) and biotinylated Versican G1 domain (G-HA02) were from Echelon Biosciences (Salt Lake City, Utah, USA). Strong anion exchange (Q) spin columns (catalog #90010), dialysis devices and cassettes with 3.5 kDa cutoff were from Thermo Pierce (Rockford, Ill., USA).

Pure HA Stock Solutions Preparation

Pure HA samples were dissolved and stored at 4° C., at concentrations of 1 mg/mL for Select-HA™ and 0.5 mg/mL for polydisperse HA, in deionized water. The concentrations of the polydisperse HA solutions were determined by weighing the dry powders for solution preparation. Considering the water content in the powder, the deviation was <5% by this method, according to Haserodt et al. (2011). The concentrations of Select-HA™ solutions were based on dissolution of the entire contents of vials containing 1 mg, where that exact weight was confirmed by the supplier using the carbazole method for solutions aliquoted and dried in the vials, and the deviation was <3%. The HA stock solutions were diluted with PBS before use.

Hyaluronan Molecular Mass Distribution Analysis

Hyaluronan was fractionated according to molecular mass by calibrated ion exchange chromatography, and the fractions were analyzed for HA content by a specific competitive Enzyme-linked Sorbent Assay (ELSA). The scheme for this HA characterization process is represented in FIG. 1 and described below in detail.

Ion Exchange (IEX) Chromatographic Fractionation of Polydisperse HA

Figure 2A:
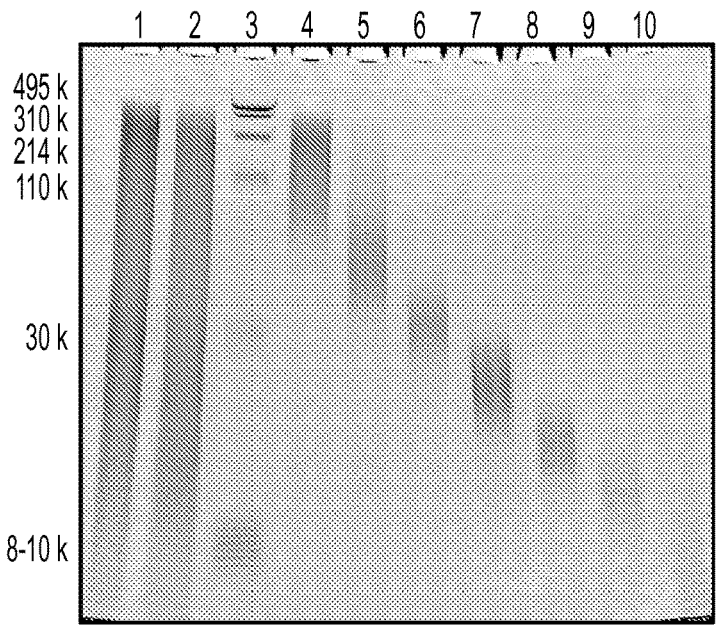
FIGS. 2A-2C show an electrophoretic analysis of a polydisperse HA sample fractionated by stepwise elution from an IEX spin column using seven NaCl solutions of increasing concentration.
Figure 2B:
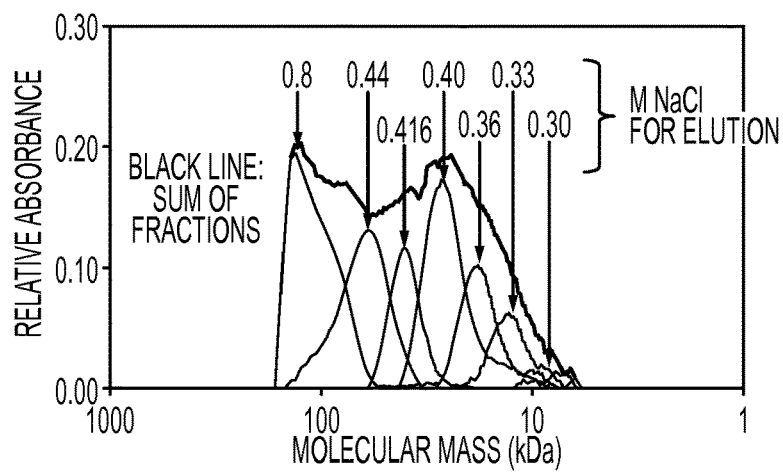
Figure 2C:
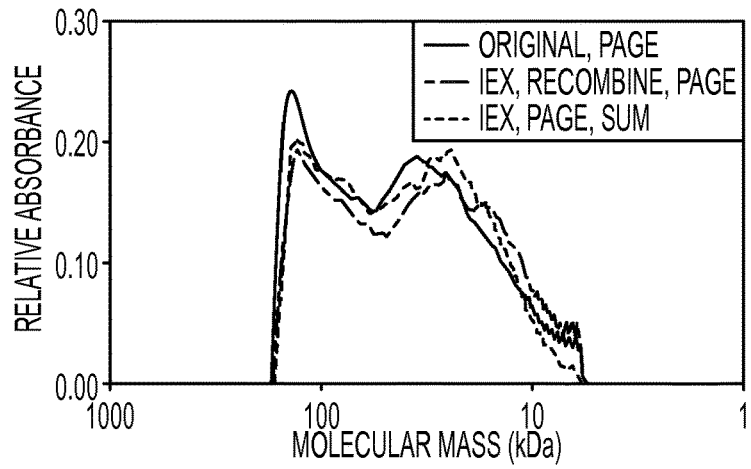
Figure 9A:
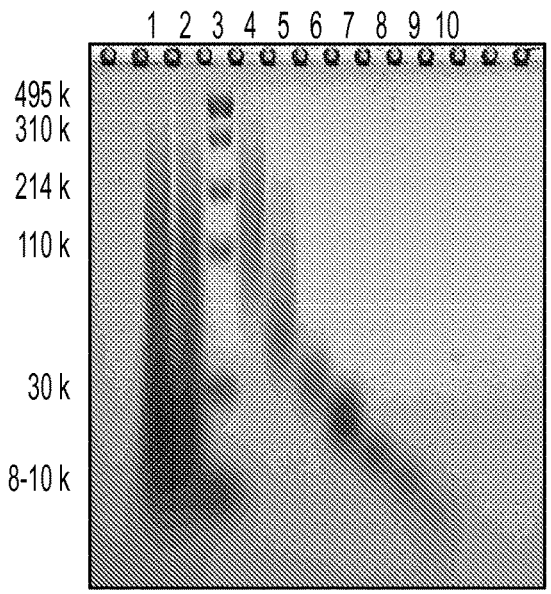
FIGS. 9A-9C show electrophoretic analysis of a polydisperse HA sample fractionated by stepwise elution from an IEX spin column using seven NaCl solutions of increasing concentration.
Figure 9B:
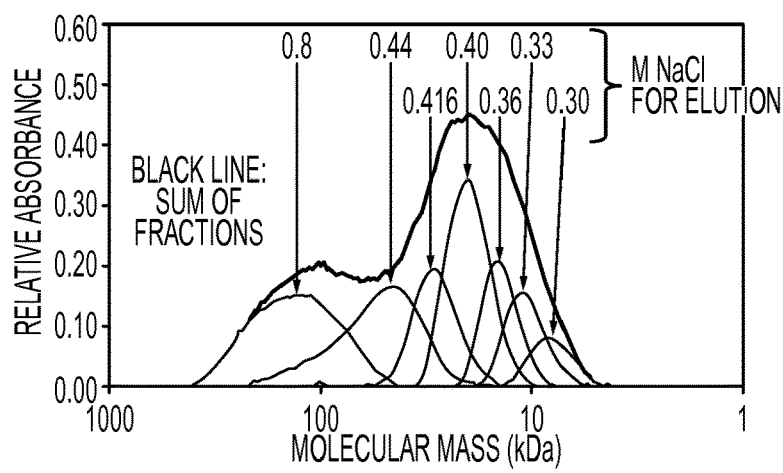

In order to establish the method, a highly polydisperse HA test sample was created by mixing equal amounts of two polydisperse purified HA samples having viscosity-average (close to weight-average) M values of 22 kDa and 112 kDa. The HA samples were separately dissolved in water at a concentration of 0.5 μg/μL. The combined sample was prepared by mixing together 20 μL (containing 10 μg HA) of each solution, and adding 0.050 M NaCl to a total volume of 800 μl. All NaCl solutions used in the ion exchange separations were prepared to an accuracy of at least three significant figures (sf) in concentration, using precise weights (4 sf) and volumetric flasks (4 sf). The M distribution of this combined sample was determined by polyacrylamide gel and agarose gel electrophoresis, with detection using STAINS-ALL dye. These methods have been previously shown to give accurate molecular mass determinations for HA within appropriate M ranges for each gel type (Cowman et al., 2011 and Bhilocha et al., 2011). FIGS. 2A-2C shows the polyacrylamide gel image, and corresponding densitometric profiles. Corresponding data for agarose gel electrophoresis are presented in FIGS. 9A-9C. Differences in profile shape are due to the relatively poorer separation of high M HA on polyacrylamide gel, and the relatively poorer separation of low M HA on agarose gel. This is analogous to the effects associated with the void and total volume peaks on gel filtration chromatographic separations, where poorly separated species elute together.

Fractionation of the HA mixture was performed using two strong anion exchange (Q) spin columns (Thermo Pierce, catalog #90010, 500 μL), each treated identically. For each step of the procedure, each column was loaded with 400 μL of sample or salt solution, then centrifuged at 400×g for 2 min for elution. Each column was pre-washed once with a 400 μL aliquot of 0.050 M NaCl. The HA sample in 0.050 M NaCl was loaded, centrifuged, and then the column was again washed once with a 400 μL aliquot of 0.050 M NaCl. The column was washed further with three aliquots of 0.200 M NaCl, which does not cause release of any pure HA of the sample, but aids analysis of impure biological HA samples by removing some impurities. To elute HA of increasing size, the column was eluted stepwise with 2×400 μL aliquots of NaCl solutions with concentrations of 0.300, 0.330, 0.360, 0.400, 0.416, 0.440, and 0.800 M (seven fraction method), or 0.360, 0.425, 0.460 and 0.800 M (four fraction method). Corresponding fractions from both columns were combined. Each combined 1.6 mL fraction was dialyzed against de-ionized water using 3.5 kDa cutoff dialysis devices (Thermo Pierce, catalog #88403), and a volume ratio of samples to dialysate of 1:26, with a total of 5 changes of dialysate over 16-18 h. The dialyzed fractions were each concentrated to a volume of approximately 200 μL using a centrifugal evaporator, using minimal heating to aid sublimation but keeping the sample cold, such that monodisperse HA subjected to the same process showed no degradation. The exact volume of each fraction was determined by liquid weight. Then these fractions were used as follows: 15% of each were taken for the Enzyme-Linked Sorbent Assay (ELSA); 20% of each were taken for electrophoresis; 50% of each were taken and added together as a combined elution named "recombine". Subsequently, 40% of the "recombine" sample was used for electrophoresis, and the rest saved for future use.

Calibration of IEX Separation by Correlation of HA Fraction Elution Conditions with Electrophoretic Determination of Average M and M Distribution The portion of each HA fraction that had been reserved for electrophoresis was concentrated to approximately 10 μL. Electrophoresis was performed using polyacrylamide (4-20% gradient) and agarose (3%) gels (FIGS. 2A and 9A), and the scanning process and the subsequent mass distribution analysis followed the methods described by Cowman et al. (2011) and Bhilocha et al. (2011). Generally, after densitometric scanning, a calibration plot of the logarithm of the HA standard molecular mass versus migration distance (pixel number in the scan data) on the gel was prepared for each gel. From the linear portion of the calibration plot, an equation was generated to allow conversion of migration distance to molecular mass for all HA sample densitometric profiles in that gel. The average M and range of M (width at half height) for each fraction have been obtained from these profiles.

Figure 3:
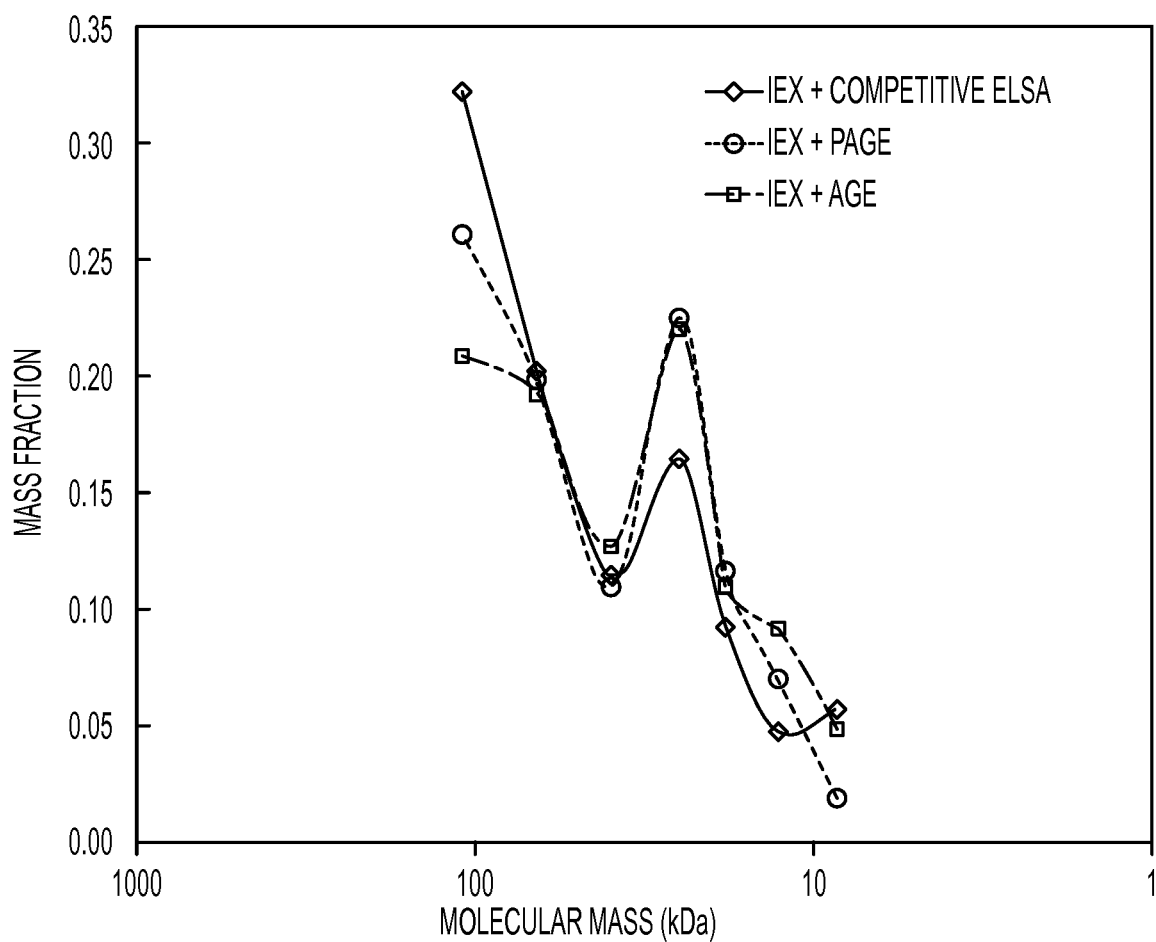
FIG. 3 is a comparison of the mass profile as a function of M (M distributions) obtained for a polydisperse HA sample by electrophoretic and IEX-ELSA methods. Each fraction was analyzed by polyacrylamide gel and agarose gel electrophoresis (the area under the densitometric curve for each fraction was determined), and by a competitive ELSA assay (ELISA-like assay). The shape of the M distribution, which can be analyzed by electrophoresis only for purified HA, is well approximated by an HA-specific quantification assay of the fractions.

The IEX method fractionates HA according to molecular mass, because the total charge of a chain depends on the number of repeating disaccharide units. Using 0.300 M NaCl, only very low M HA (ca. 5-9 kDa) could be eluted. Using subsequent steps of 0.330, 0.360, 0.400, 0.416, and 0.440 M NaCl allowed elution of HA fractions with increasing average M. A single step of 0.800 M NaCl eluted all remaining HA with M above ca. 80 kDa. FIGS. 2A and 2B, 9A and 9B show the electrophoretic gel results and densitometric scans for the fractions. The densitometric scans of the stained gels were used to determine the M range and the average M for each fraction (see Table 1 below), and the portion of the total stained area (=mass ratio) for each fraction based on the relative area under each peak in the densitometric profile (FIG. 3).

The polydispersity of the HA fractions obtained by IEX varies with M, since the relative difference in total charge decreases with increasing chain length. In the very low M range, HA is separated into fractions with quite low polydispersity, indicated by the narrow bands observed by electrophoresis. As the concentration of the eluting salt solution increases, the corresponding HA fractions become broader in M distribution. It can be seen that at 0.360 M NaCl, only HA between ca. 13-20 kDa came out, and at 0.416 M NaCl, HA between ca. 32-47 kDa was washed out, but 0.440 M NaCl then eluted HA of ca. 43-74 kDa. The fractionation of higher M HA became even more sensitive to the salt concentration, and thus size-dependent fractionation on the IEX spin column was relatively poor for HA larger than about 100 kDa. Using 0.500 M NaCl eluted HA up to at least ca. 2 MDa (data not shown). 0.8 M NaCl was used to be certain to elute any HA of larger size.

The same IEX fractionation process was conducted six times with the same sample to determine the reproducibility of the fractionation process. Each time the average M and range of M for each fraction was obtained from its electrophoretic result. The densitometric scan of the stained gel allowed determination of the average M of each fraction, and the portion of the total stained area (=mass percent) for each. The reproducibility of the molecular mass correlation with NaCl concentration needed for elution, used to calibrate the IEX column characteristics, is presented in Table 1. Table 2 presents the percent of HA mass found in each fraction, based on the summed area under each peak in the densitometric profile, for the seven fraction method.

TABLE 1

HA Sample Fractionation by IEX (7 fraction method and 4 fraction method)

| IEX Fraction (M NaCl) | HA average M (kDa) | HA M range (kDa) (width at half height) |
|---|---|---|
| 0.300 | 7 ± 1 | 5 ± 1 to 9 ± 2 |
| 0.330 | 11 ± 1 | 9 ± 1 to 14 ± 2 |
| 0.360 | 16 ± 2 | 13 ± 2 to 20 ± 3 |
| 0.400 | 25 ± 2 | 19 ± 2 to 33 ± 3 |
| 0.416 | 38 ± 3 | 32 ± 2 to 47 ± 4 |
| 0.440 | 61 ± 10 | 43 ± 4 to 74 ± 12 |
| 0.800 | *150 (>80) | 79 ± 16 and above |
| 0.360 | 12 | 7 to 21 |
| 0.425 | 35 | 22 to 56 |
| 0.460 | 80 | 57 to 114 |
| 0.800 | *155 (>80) | 108 and above |

*data obtained from the results of 3% agarose gel electrophoresis.

TABLE 2

Mass distribution of HA Sample in IEX fractions by PAGE versus ELISA

| IEX Fraction (M NaCl) | HA mass percent from PAGE | HA mass percent from ELISA |
|---|---|---|
| 0.300 | 1.9 | 5.4 |
| 0.330 | 7.0 | 4.5 |
| 0.360 | 11.7 | 8.8 |
| 0.400 | 22.5 | 15.8 |
| 0.416 | 11.0 | 10.9 |
| 0.440 | 19.9 | 19.4 |
| 0.800 | 26.1 | 30.8 |

Figure 10A:
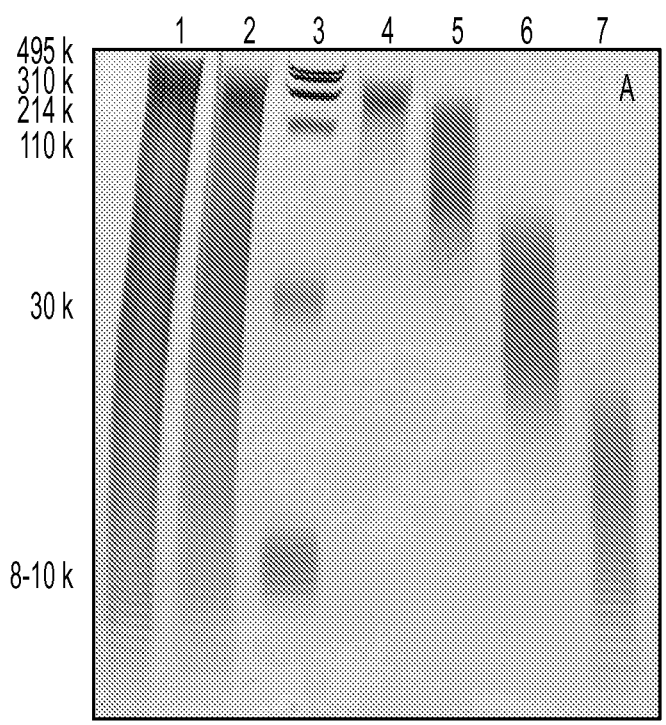
FIGS. 10A and 10B show the M distribution of HA fractions obtained by IEX can be controlled.
Figure 10B:
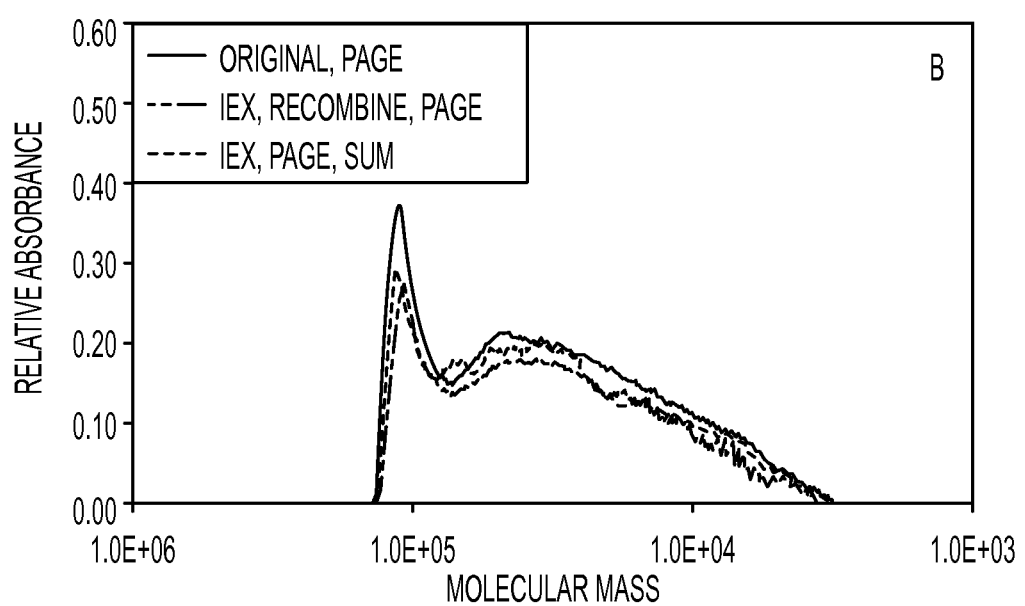

The IEX elution step gradient could be varied to obtain HA with specific controlled size ranges. FIG. 10A and Table 1 show the results and characteristics of the same polydisperse HA sample described above, after separation into only 4 fractions using NaCl steps of 0.360, 0.425, 0.460, and 0.800 M. FIG. 10B affirms the successful fractionation and absence of sample loss, and Table 1 presents the characteristics of this fractionation set. Other specific desired HA fractionation patterns could be developed using an IEX spin column eluted with salt solutions of appropriate concentrations.

Experimental Considerations Related to Calibrated IEX Fractionation of HA

Figure 9C:
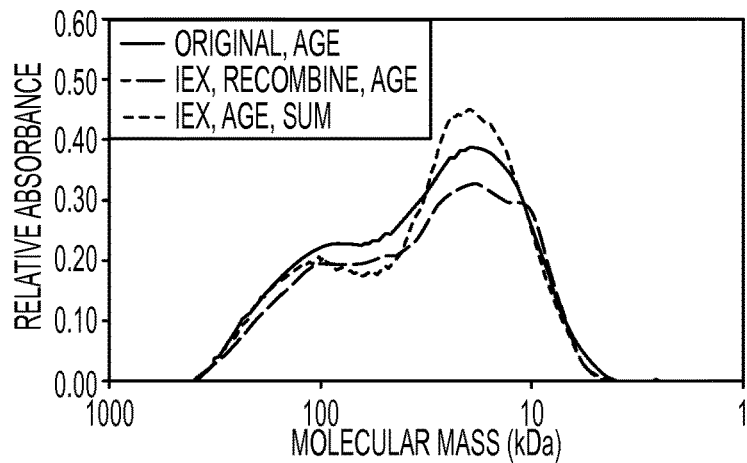

The question of possible HA loss or degradation during the IEX fractionation process, especially the preferential loss of specific sizes of HA, was addressed in two ways. First, an equal portion of each HA fraction obtained after the IEX separation was removed, and a recombined sample was obtained by mixing them together. The recombined sample was dialyzed to remove salt, concentrated, and co-electrophoresed on polyacrylamide or agarose gel with the original sample (FIGS. 2C, 9C and 10B). Within normal limits of reproducibility in densitometric analyses of HA by this method, the recombined sample was the same as the original sample on both polyacrylamide and agarose gel. Second, equal portions of the HA fractions were co-electrophoresed with the original and recombined samples, and the densitometric profiles of the fractions were summed. The summed profile was also identical with that of the original sample within experimental uncertainty. Therefore, there was no discernible total loss or preferential loss of any size HA during the IEX fractionation procedure, and no apparent degradation of HA. Analysis of the HA fractions by electrophoresis is not routinely necessary, but has been performed in this example of highly polydisperse pure HA in order to establish correlation data for the average M and range of M present for HA eluted at each salt concentration.

The size calibration of fractions obtained using pure HA, eluted at a given NaCl concentration, can be applied to the analysis of less pure HA from biological fluids and tissues, when separated and analyzed by the same procedure. In order to maintain reproducibility and calibration, several experimental details must be standardized and maintained constant. The centrifugal force applied to the IEX spin column needs to be kept constant and is recommended to be no higher than 400×g. Higher force was found to result in premature release of HA from the column. The temperature needs to be kept constant. Elution of HA using cold salt solutions occurred at lower salt concentration than observed with room temperature solutions. For some IEX column lots, we found an unknown (possibly cationic) species may be shed from the column during sample elution, and later cause precipitation of HA following fractionation and dialysis. It is therefore recommended to prewash the IEX column three times with 400 μL of 0.800 M NaCl, and then to re-equilibrate the column using five washes with 400 μL of 0.050 M NaCl, before use. HA fractions need to be completely dialyzed to remove salt, before concentration and electrophoresis. Concentration in the presence of high salt has been observed to result in HA degradation. Electrophoresis in the presence of residual salt concentrations greater than about 0.15 M causes aberrant migration.

Quantitative Analysis of HA Fractions by Competitive ELSA Assay and Comparison with Electrophoretic Analysis In order to quantify the mass of HA eluted at each NaCl concentration, a specific competitive ELSA (ELISA-like but using a specific binding protein) assay (type K-1200, from Echelon Biosciences) was employed. An equal portion (30 μL) of each fraction (from the 200 μl, samples after dialysis) was mixed with Reagent Diluent (provided in the kit) to a final volume of 500 μL. This was the 1× sample. A 125 μL portion was then removed and diluted three-fold with Reagent Diluent to 375 μL. This is the (1/3)× sample. A 125 μL portion of the (1/3)× sample was further diluted to 375 μL to make a (1/9)× sample. Each sample was analyzed in duplicate. The assay procedure followed the instructions within the kit. The final signal was collected after 45 min substrate incubation, using a microplate reader (SpectraMax M2, Molecular Devices). The HA concentration for each fraction isolated by the ion exchange purification method was determined and then used to calculate the percent of the mass of HA found in each fraction, relative to the whole sample (sum of all fractions). Results are provided in Table 2. FIG. 3 presents a comparison of the results from the ELSA assay with the results from densitometric analysis of the electrophoretic gels. There is excellent agreement in the shape of the M distribution of HA analyzed by the two methods.

Since imperfectly purified HA isolated from limited biological sources will not allow electrophoretic analysis with nonspecific staining, or blotting and specific detection that cannot reveal HA less than 20 kDa and cannot properly quantitate HA less than 150 kDa, the above demonstration of equivalence for pure HA is essential. It shows that the M distribution of HA in biological samples can be accurately determined using the ion exchange fractionation and specific competitive ELISA-like assay.

Isolation and Molecular Mass Distribution Determination for Human Milk HA

1. HA was isolated from human milk using essentially the method described by Hill et al. (2013). A 10 ml aliquot of milk was digested by addition of proteinase K to a concentration of 0.5 μg/μl, and then incubation at 60° C. overnight. To remove lipids, the digested sample was centrifuged for 10 min at 4000×g to separate the lipids, and the lower aqueous layer was collected. It was transferred to a 10 ml dialysis cassette with a 2 kDa cutoff, and exhaustively dialyzed against 2l of deionized water, changed five times over 24 h. The dialyzed sample was concentrated to approximately 1.6 ml, using a centrifugal evaporator, and then heated to 90° C. for 10 min to deactivate any remaining protease. This was the incompletely purified HA sample to be subjected to molecular mass distribution analysis.

One-fifth of the isolated milk HA was retained for analysis of the total HA content by ELISA-like assay. The remaining HA sample was fractionated according to M using anion exchange. It was diluted with deionized water to a total volume of 1.6 ml, then mixed with 2 M NaCl to reach a final NaCl concentration of 0.05 M. It was fractionated using four strong anion exchange spin columns (Thermo Pierce, catalog #90010, 500 μl) treated identically for one-fourth of the HA sample each. For each step of the procedure, each column was loaded with 400 μl of sample or salt solution, then centrifuged at 400×g for 2-3 min for elution. Each column was pre-washed once with a 400 μl aliquot of 0.05 M NaCl. The HA sample in 0.05 M NaCl was loaded, centrifuged, and then the column was again washed once with 400 μl of 0.05 M NaCl. The column was washed further with three aliquots of 0.2 M NaCl. To elute HA of increasing size, the column was eluted stepwise with 2×400 μl aliquots of NaCl solutions with concentrations of 0.30, 0.33, 0.36, 0.40, 0.416, 0.44, and 0.80 M. Corresponding fractions from the four columns were combined. Each 3.2 ml pooled fraction was first concentrated to ca. 2 ml, then dialyzed against deionized water using 3.5 kDa cutoff dialysis devices, and a volume ratio of samples to dialysate of 1:22, with a total of 4 changes of dialysate over 10 h. The dialyzed fractions were each concentrated to a volume of approximately 100 μl using a centrifugal evaporator.

Figure 5A:
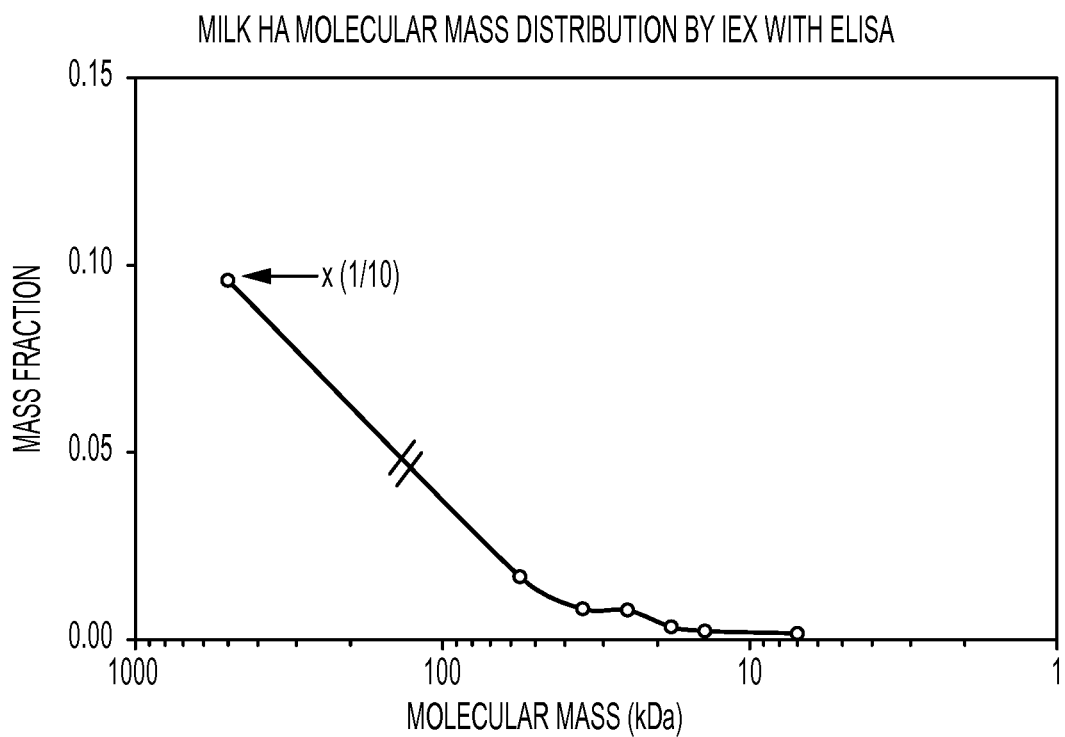
FIGS. 5A and 5B are graphs showing the mass profile as a function of M (M distribution) for HA isolated from a sample of human milk, fractionated into seven fractions by IEX and assayed by competitive ELISA-like assay (FIG. 5A) and for the twenty partially purified human milk HA samples after fractionation into four fractions by IEX, and analysis by competitive ELSA (ELISA-like) assays (FIG. 5B). The mass ratio of the high M HA eluted at 0.800 M was scaled to 1/10 for improved visualization of the low M HA fractions. The average M (ca. 440 kDa) for the 0.800 M HA fraction from milk was separately determined by agarose gel electrophoresis.

The seven milk HA fractions were analyzed by competitive ELISA-like assay (type K-1200, from Echelon Biosciences). FIG. 5A is a graph of the mass fraction of the total HA that was found in each of the seven fractions, versus the weight-average molecular mass of the HA in each fraction, previously calibrated using purified HA. The 0.8 M NaCl fraction contained about 96% of the total HA. The remaining 4% of the HA was approximately 20-60 kDa in molecular mass. This includes ca. 35 kDa HA known to be active in protection of the human intestinal epithelium by stimulating expression of antimicrobial peptides (Hill et al., 2012).

The combination of IEX fractionation of HA by size, and specific determination of HA content in each fraction by a competitive ELISA-like assay, was able to quantify the fraction of milk HA present as a low M species, which has been identified as a bioactive signal molecule with protective properties for the intestinal epithelium.

2. The twenty human milk samples were collected, analyzed for HA concentration by a competitive ELSA assay (Echelon Biosciences), and frozen for later use. HA was isolated using essentially the method described by Hill et al. (2013). Bacterial contamination was avoided by using only pre-autoclaved tubes, pipettes, and labware. Frozen milk samples were defrosted. An aliquot of 20-30 mL per sample was heated in boiling water for 10 min, then cooled in an ice water bath for 10 min. Protein was digested by addition of proteinase K (Roche Applied Science, catalog #03115828001) to a final concentration of 0.5 mg/mL, and then incubation at 60° C. overnight. To remove lipids, the samples were cooled for 10 min in an ice water bath and centrifuged for 15 min at 3000×g at 4° C., and the lower aqueous layer in each tube was collected. The centrifugation was repeated once to more completely remove lipid. The aqueous solutions were further centrifuged at 25,000×g for 10 min at 4° C. to remove any particulate material, and then heated in a boiling water bath for 10 min to deactivate any remaining protease. Samples were cooled to room temperature in an ice water bath, then centrifuged again at 25,000×g for 10 min at 4° C. Each clarified sample was transferred to a 50 mL dialysis cassette with 3.5 kDa cutoff, and exhaustively dialyzed against five changes of 4 L deionized water over 16 h. Dialyzed samples were centrifuged at 25,000×g for 10 min at 4° C. to remove any particulate matter, then concentrated to approximately 4 mL, using a centrifugal evaporator. This was the incompletely purified HA sample to be subjected to molecular mass distribution analysis. An aliquot containing at least about 300 ng HA was taken from each sample for later concentration determination. The remaining sample was made 0.050 M in NaCl by addition of a 0.200 M stock, and adjusted to a volume of 4 mL, then stored frozen at −20° C.

HA samples were fractionated according to M using ion exchange chromatography (IEX). Each sample was fractionated using ten strong anion exchange mini spin columns treated identically. For each step of the procedure, each column was loaded with 400 μL of sample or salt solution, then centrifuged at 400×g for 2-3 min for elution. The procedure for handling the milk HA samples on IEX was essentially the same as described above for pure HA. One sample was analyzed by the seven fraction method, and twenty samples were analyzed by the four fraction method. Corresponding fractions from the ten columns used for each sample were combined. Each 8 mL pooled fraction was transferred to a 12 mL, 3.5 kDa cutoff, dialysis cassette, and the fractions for each sample were dialyzed together against 4 L deionized water with a total of five changes of dialysate over 16 h. The dialyzed fractions were each concentrated to a volume of approximately 1 mL using a centrifugal evaporator, transferred to a microcentrifuge tube, stored frozen if necessary, and then taken to dryness in a centrifugal evaporator. Tubes were stored at −20° C. until assayed.

Preliminary experiments had shown that the levels of low M HA in human milk were only about 4-5% of the total HA. All of the higher M HA ca. 110 kDa) would be present in the 0.800 M NaCl fraction. For milk samples with sufficient HA based on the initial sample HA assay, the 0.800 M fraction was dissolved in water, and an appropriate volume containing about 5 μg HA was kept for analysis by 1% agarose gel electrophoresis, before and after digestion of HA using the HA-specific hyaluronidase from *Streptomyces hyaluronolyticus* (Seikagaku Corporation) at a ratio of 0.25 units per μg HA, at 37° C. for 4 h. The M distribution of HA in this fraction was obtained by subtracting the densitometric profile of the digested sample from that of the undigested. The remainder of the 0.800 M fraction was appropriately diluted into Reagent Diluent used in the ELSA assay (Echelon Biosciences). Lower M HA fractions eluted from the IEX spin columns at lower salt concentrations were directly dissolved in 400 μL Reagent Diluent, and not analyzed by electrophoresis due to the low HA contents and high level of co-purifying contaminants that preclude detection of HA by staining after electrophoresis.

The HA fractions from each milk sample were analyzed by competitive ELSA assay. For a 25 mL milk sample at an average HA concentration of about 250 ng/mL, the expected mass of low M HA (<ca. 100 kDa) was only about 250-310 ng, distributed relatively evenly among the three low M fractions. The ELSA assay preferably has HA concentrations of about 100-1000 ng/ml, and requires 0.1 mL per well, so a minimum of 10 ng is needed per well and duplicate analysis requires at least 20 ng. Assay at multiple dilutions further increases the amount of HA needed. In order to bring most test samples to a point closer to the midpoint of the standard curve, they were spiked with a known amount of pure HA (polydisperse HA with 59 kDa average M, from Lifecore Biomedical), and the appropriate spike concentration as determined on the same assay plate was subtracted from corresponding sample values.

Specific HA Isolation from Human Milk HA Fractions

At room temperature, 150 μL of 10 mg/mL streptavidin-coated magnetic bead suspension (M-280, Life Technologies) was pre-cleaned 3 times with 150 μL, PBS 0.05% TWEEN (polyoxyethylene sorbitan monolaurate), following the manufacturer's instructions. An 80 μL, aliquot of low M milk HA (estimated to contain ~0.3 μg HA in deionized water), obtained by 0.425M NaCl elution of No. 14 human milk HA from IEX and subsequent dialysis, was mixed with 10 μL of 0.75 μg/μL biotinylated versican G1 domain (bVG1, Echelon Bioscience) in PBS for 3 h at room temperature to saturate HA chains with bVG1. The 90 μL mixture was then mixed with the washed beads for 45 min to let the HA-bVG1 complex bind to the beads. After that, the beads were collected by magnet and washed 3 times with 150 μL PBS 0.05% TWEEN each time. Deionized water (70 μL) was then added to the beads and heated at 95° C. for 15 min to release HA from the beads. The supernatant was collected and the elution process was repeated once using another 50 μL water. After that, the two HA-containing solutions were merged and concentrated to about 20 μL. Proteinase K (Roche) was added to the HA solution to a concentration of 1 μg/μL and the mixture was kept at 60° C. for 3 h to digest any released bVG1. The sample was concentrated to ~10 μL before electrophoresis on the 4-20% polyacrylamide gel (Life Technologies). The electrophoresis process was as previously described (Cowman et al., 2011; Bhilocha et al., 2011).

RESULTS

HA in human milk is present at very low concentration (generally, ca. 100-1000 ng/mL (Hill et al., 2013), and has proven difficult to purify from all contaminants using standard HA isolation protocols. The procedures employed included removal of proteins by protease treatment, removal of lipids, and removal of dialyzable components. Such procedures do not remove certain contaminants that interfere with detection of HA on electrophoretic gels for size determination. These contaminants can include unsulfated chondroitin, sulfated glycosaminoglycans, protease-resistant proteins, and other unknowns, possibly including nucleic acids. As an alternative, a size- and charge-dependent separation method, coupled with specific quantification, was developed. Ion exchange (IEX) chromatography on a strong anion exchange (Q) resin in a spin column format was used to remove sulfated glycosaminoglycans and to separate HA according to size, using a step gradient in NaCl for elution. Each fraction was dialyzed to remove salt, then analyzed for HA content using a competitive specific ELSA assay, since contaminants such as chondroitin that are still not removed by the IEX will not be detected by the ELSA. The IEX separation was calibrated using pure HA.

HA in Milk is not Degraded by the Isolation and Fractionation Method

Figure 4:
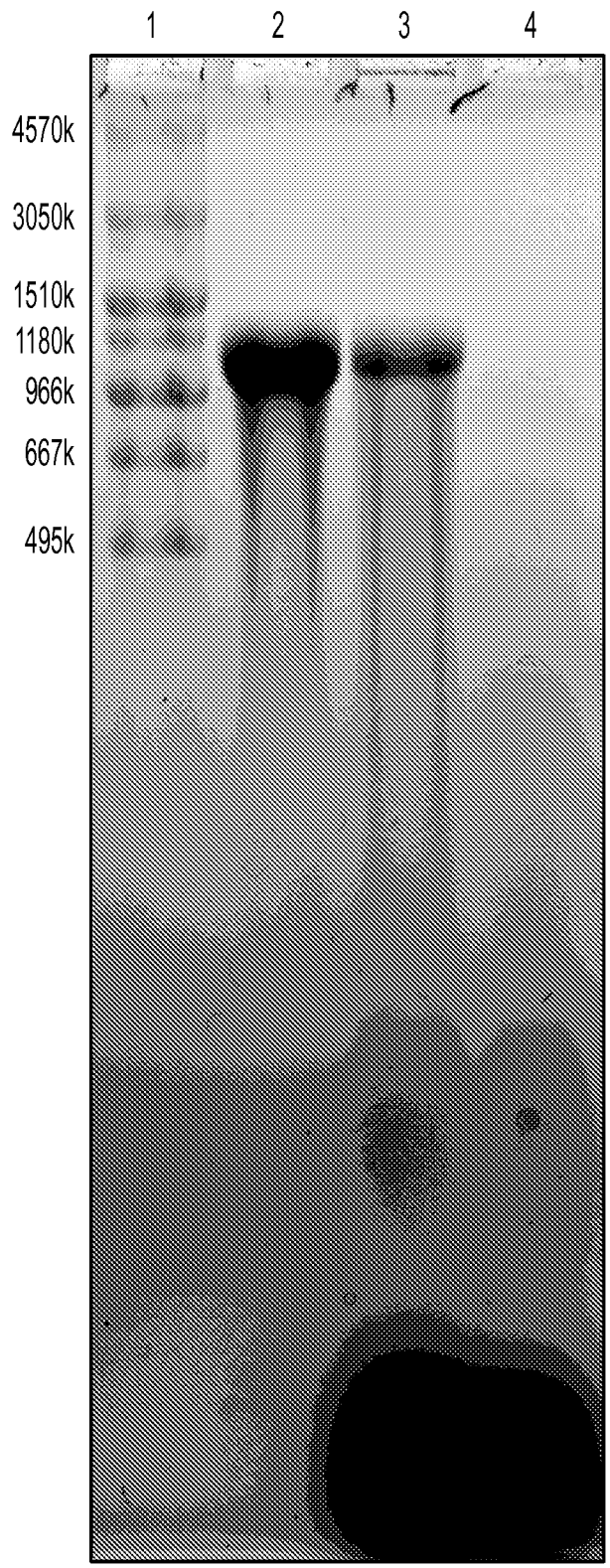
FIG. 4 is a polyacrylamide gel electrophoresis of low polydispersity 1000 kDa SELECT-HA, that was added to milk and subjected to both purification and IEX fractionation steps, and that shows little or no degradation after the entire procedure. Lane 1: MegaLadder and HiLadder HA standards. Lane 2: untreated 1000 kDa SELECT-HA, 1.5 µg. Lane 3: high M HA component (0.800 M NaCl elution) isolated from 3 mL milk spiked pre-isolation with 1.5 µg 1000 kDa SELECT-HA. Lane 4: high M HA component (0.800 M NaCl elution) isolated from 3 mL milk.

The question of possible HA degradation during the isolation and IEX procedures was examined by spiking HA standards into milk, and subjecting the sample to purification and fractionation. FIG. 4 shows that 1000 kDa HA, added to milk and subjected to both purification and IEX steps, shows little or no degradation after the entire procedure. A similar purification method has been applied elsewhere (Tolg et al., 2012) in the purification of HA from rat skin, yielding HA with average M of approximately 6000 kDa. The procedure used here appears to cause no significant degradation or loss of either high M or low M HA.

HA Recovery from Milk Following Isolation and Fractionation is High

The question of HA recovery through the procedure was addressed by measuring the total HA content in raw milk samples, and then the total HA content in the final IEX fractions. The overall recovery averaged approximately 82%±23% (apparent range 53-124%). The average recovery of milk HA during the IEX step alone was 103%±35%. Spiked 1.7 MDa pure HA added into milk had a recovery of ca. 75% in a control experiment (data not shown).

The IEX Fractionation Removes Sulfated Glycosaminoglycans from Milk HA

Figure 11:
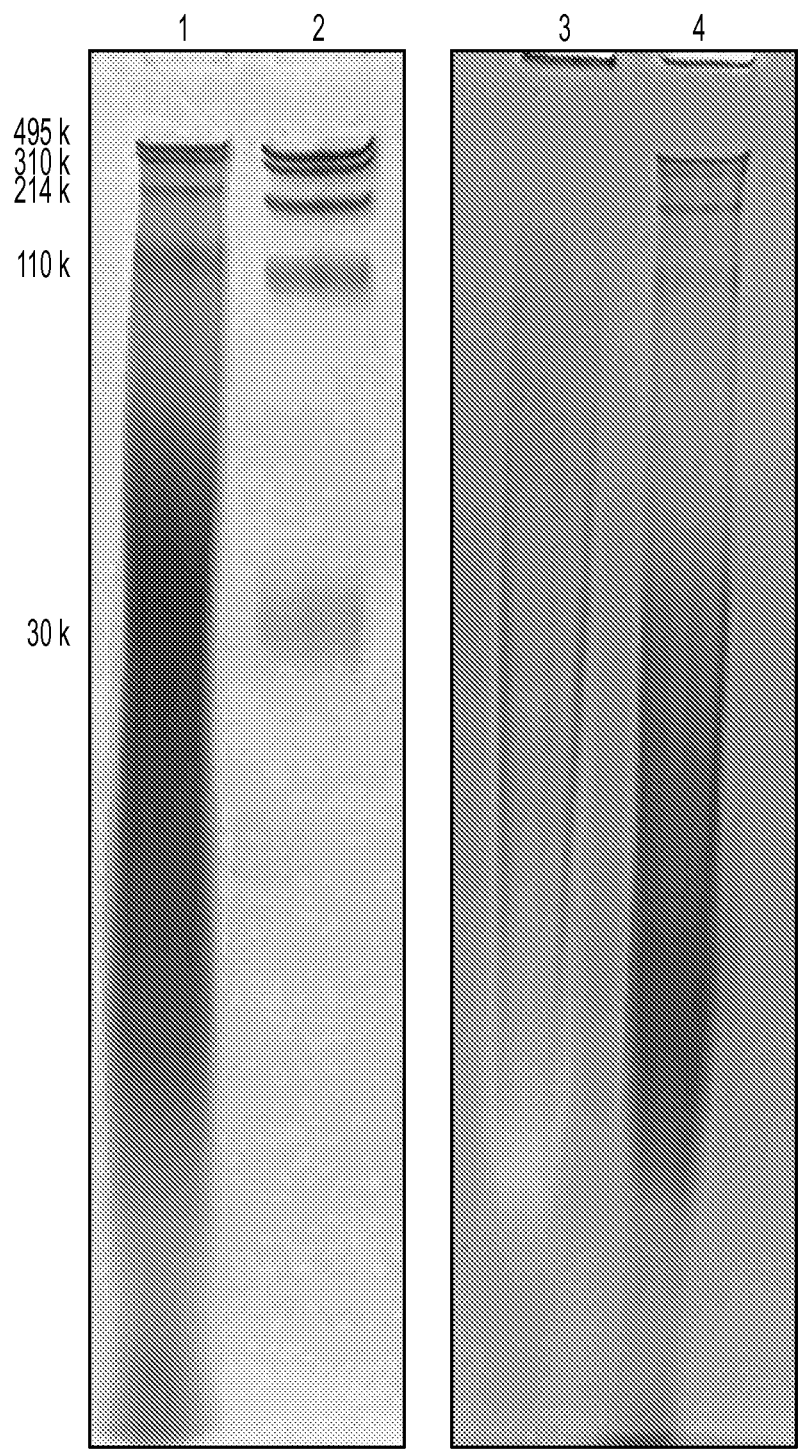
FIG. 11 shows that ion exchange chromatography separates milk HA from sulfated glycosaminoglycans. Samples were electrophoresed on a 4-20% polyacrylamide gel, and stained with STAINS-ALL dye. Lane 1: Milk was spiked with LoLadder HA standard and purified by protein digestion and lipid removal. Spiked HA was recovered without degradation, and was accompanied by non-HA components. The high M component of milk HA co-migrates with the highest M SELECT-HA band. Lane 2: LoLadder HA containing HA molecular mass markers 495, 310, 214, 110, and 30 kDa. Lane 3: Sulfated glycosaminoglycans were eluted from IEX with 1.5 M NaCl after removal of non-HA components with 0.30 M NaCl, and removal of HA with 0.70 M NaCl. Lane 4: Milk HA obtained in a 0.70 M NaCl elution from IEX. Stained material migrating more rapidly than the 30 kDa HA marker is primarily non-HA impurities including chondroitin.

The behavior of sulfated glycosaminoglycans on the IEX system was examined first with pure chondroitin 4-sulfate and dermatan sulfate, and then using milk HA. The sulfated glycosaminoglycans are well separated according to size and charge on polyacrylamide gel electrophoresis, and can be differentiated from HA by the different characteristic color of bands stained with STAINS-ALL dye (blue for HA or chondroitin, purple for chondroitin sulfate or dermatan sulfate, and yellow-orange for heparan sulfate). Low M chondroitin 4-sulfate fragments were observed to be eluted from the IEX column used in the present study by an NaCl concentration of 0.90-1.0 M. Chondroitin 4-sulfate polymers were eluted at approximately 1.1 M NaCl, and a concentration of 1.5 M NaCl was adopted for complete elution of the sulfated glycosaminoglycans chondroitin 4-sulfate, chondroitin 6-sulfate, and dermatan sulfate. For partially purified milk HA (containing [nonsulfated or undersulfated] chondroitin and sulfated glycosaminoglycans), elution from the IEX column with 0.800 M NaCl will release even very high M HA, but no normally sulfated glycosaminoglycans. The more highly charged sulfated glycosaminoglycans can be eluted with 1.5 M NaCl, as seen in FIG. 11.

Molecular Mass Distribution of HA from Human Milk

It was observed that conducting a fractionation protocol using a given IEX column type and specific set of NaCl concentrations led to highly reproducible results. The calibration of the IEX column, based on elution of pure HA at a given NaCl concentration, can thus be applied to the analysis of less pure HA from biological fluids and tissues, when separated and analyzed by the same procedure.

The result of milk HA characterization is presented in Table 3. The measured HA concentrations are highly disperse, ranging from 70 to 2740 ng/mL, with an average HA concentration of 250±120 ng/mL, excluding two high values (1370, 2740) which exceeded two standard deviations from the mean of the other samples.

TABLE 3

Results from Analysis of Twenty Human Milk HA Samples

| Milk source | [HA] (ng/ml) | Milk volume used (mL) | Milk HA used (μg) | Recovery (%) | Mw of 0.800 M elution (kDa) |
| --- | --- | --- | --- | --- | --- |
| 1 | 138 | 25 | 3.5 | 53.2 | — |
| 2 | 135 | 25 | 3.4 | 92.3 | — |
| 3 | 208 | 25 | 5.2 | 107.8 | 358 |
| 4 | 66 | 25 | 1.7 | 65.2 | — |
| 5 | 1374 | 8 | 11.0 | 62.1 | 331 |
| 6 | 385 | 20 | 7.7 | 51.9 | 479 |
| 7 | 252 | 25 | 6.3 | 62.9 | 410 |
| 8 | 89 | 14 | 1.2 | 72.8 | — |
| 9 | 353 | 27 | 9.5 | 54.9 | 557 |
| 10 | 262 | 22 | 5.8 | 124.1 | 464 |
| 11 | 203 | 25 | 5.1 | 103.6 | 471 |
| 12 | 127 | 25 | 3.2 | 103.8 | — |
| 13 | 331 | 27 | 8.9 | 75.8 | 400 |
| 14 | 2736 | 28 | 76.6 | 101.4 | 514 |
| 15 | 159 | 19 | 3.0 | 52.2 | — |
| 16 | 343 | 22 | 7.5 | 63.5 | 434 |
| 17 | 263 | 25 | 6.6 | 103.0 | — |
| 18 | 459 | 16 | 7.3 | 96.8 | 477 |
| 19 | 324 | 27 | 8.7 | 89.1 | 438 |
| 20 | 405 | 25 | 10.1 | 100.3 | 407 |

Figure 5B:
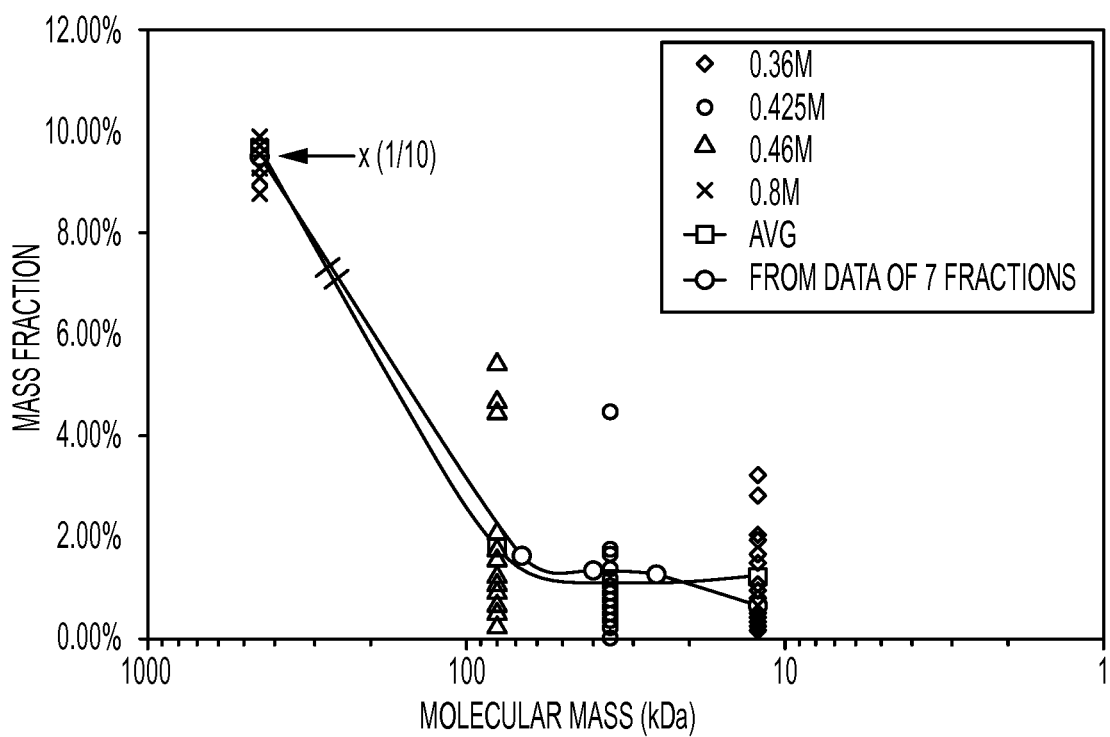

Each milk HA sample was partially purified by digesting proteins and removing lipids and other small molecules. After saving a small portion for ELSA to determine the total HA concentration, the remaining sample was further purified using the IEX spin column, by washing with low salt to remove some impurities that were unbound or weakly bound. One milk HA sample was analyzed by the seven fraction method. FIG. 5B shows the mass fraction of the total HA that was found in each of the seven fractions, versus the weight-average molecular mass of the HA in each fraction, previously calibrated using purified HA. The 0.800 M NaCl fraction contained about 96% of the total HA. The remaining 4% of the HA was approximately 20-60 kDa in molecular mass. The mass fraction of the high M HA eluted at 0.800 M was scaled to 1/10 for improved visualization of the low M HA fractions. M used for the 0.800 M NaCl fraction was from electrophoretic analysis described below.

Twenty samples of milk HA were subsequently fractionated by the four fraction method, using stepwise elution with increasing salt concentrations of 0.360, 0.425, 0.460 and 0.800 M. Based on calibration of the method using pure HA, the molecular mass distribution in these fractions is as follows: 0.360 M yields HA≤ca. 20 kDa, 0.425 M yields HA of ca. 20-60 kDa, 0.460 M yields HA of ca. 60-110 kDa, and 0.800 M yields HA ca. 110 kDa. The milk HA fractions were analyzed by a competitive ELSA assay. For the twenty milk samples analyzed, the low M (110 kDa) HA comprised only about 5% of the total mass on average, while the higher M HA was 95%. The M≤20 kDa, 20-60 kDa, and 60-110 kDa fractions respectively contained only 1.5%, 1.4% and 2% of the total HA on average. Results are shown in FIG. 5B. The mass fraction of the high M HA eluted at 0.800 M was scaled to 1/10 for improved visualization of the low M HA fractions. The solid curve is produced to fit the average mass ratio of each fraction. There is excellent agreement between the molecular mass distribution patterns obtained using the seven fraction method and the four fraction method.

Figure 6:
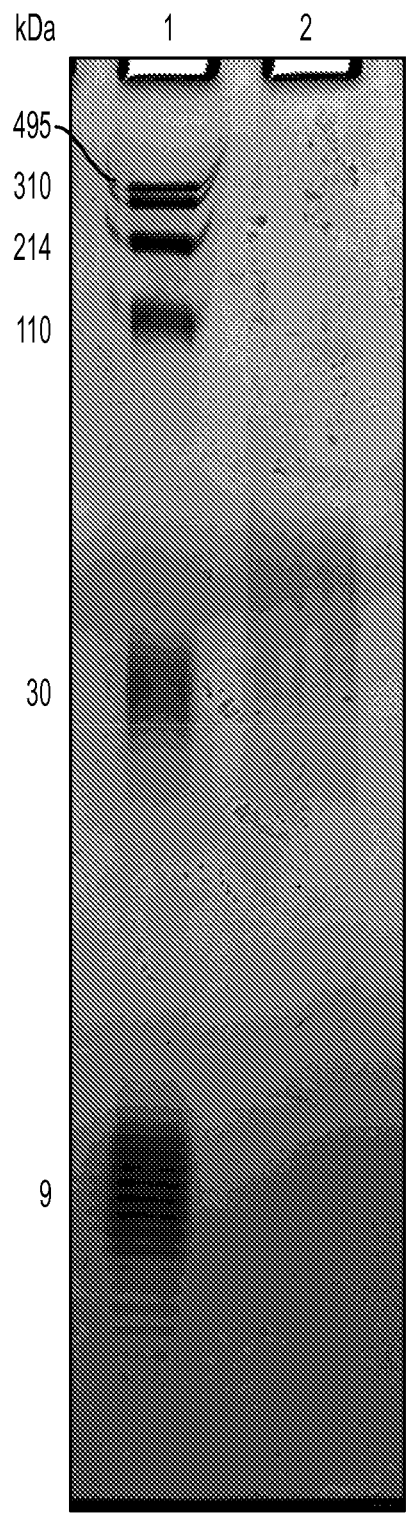
FIG. 6 shows specific isolation of low M HA from human milk, analyzed by 4-20% polyacrylamide gel electrophoresis. Lane 1: Loladder containing HA molecular mass markers 495, 310, 214, 110, and 30 kDa, in addition to purified 7.6-10 (average ca. 9) kDa HA. Lane 2: milk HA from a 0.425 M NaCl elution from IEX, captured by specific binding to bVG1 (biotinylated versican G1 domain) and streptavidin-coated magnetic beads.

Pure polydisperse HA has been shown to suffer no degradation and to be obtained in ~80% recovery without preferential size loss after the whole isolation process (data not shown). To verify that the ELSA-detected contents of low M HA in milk samples were not artifacts, and that the HA eluted at a given salt concentration had the appropriate M determined by the calibration procedure, one of the 0.425 M milk HA fractions was subjected to HA-specific isolation. The specific isolation method was developed by analogy to pull down techniques by using biotinylated versican G1 domain (bVG1) and streptavidin-coated magnetic beads. The bVG1 was first incubated with the sample solution to specifically capture and saturate the HA chains in order to obtain strong target binding, then the beads were added to the mixture to pull down the HA-bVG1 complex. After washing the beads, HA and bVG1 were released by heating, and the bVG1 was digested with Proteinase K before electrophoresis. The result of the isolation is shown in FIG. 6. The 0.425 M fraction contained HA within the range of ~25-60 kDa, which is consistent with the calibrated M range of the corresponding pure HA elution.

Figure 7:
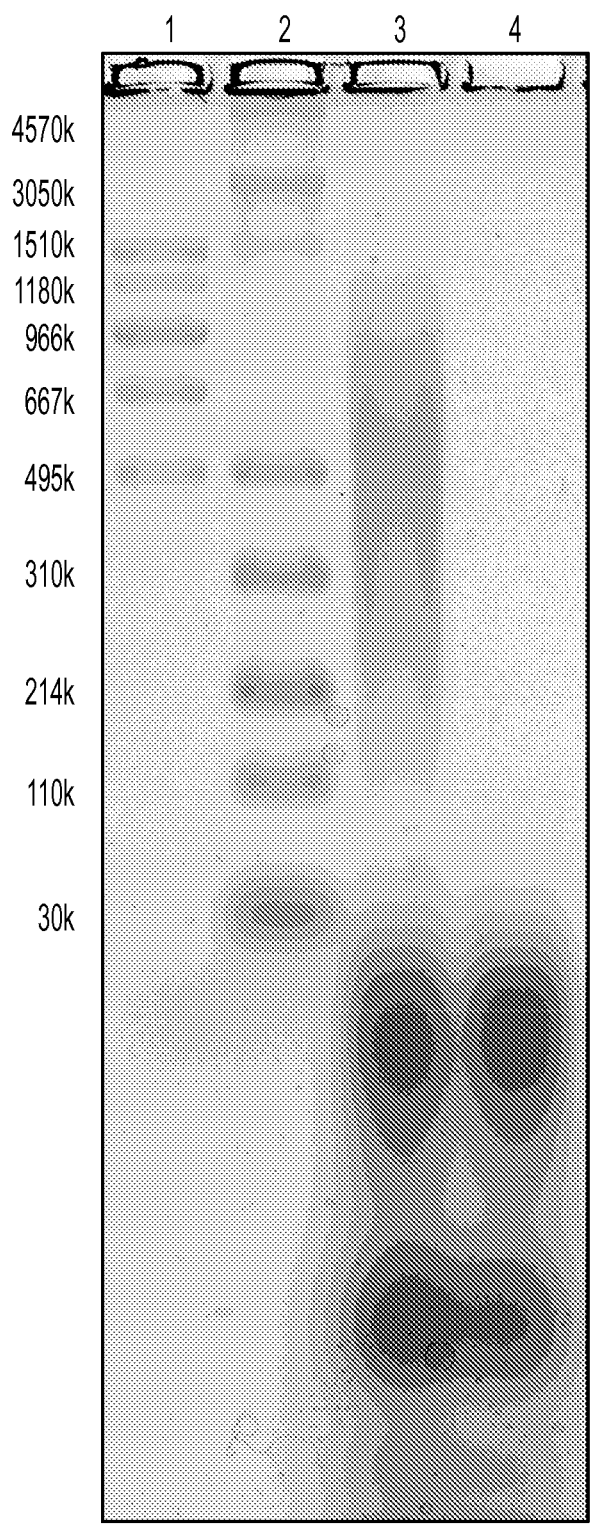
FIG. 7 shows the M distribution for the 0.800 M HA fraction from human milk sample No. 14 by 1% agarose gel electrophoresis. Lane 1: Hiladder, containing HA molecular mass markers 1510, 1180, 966, 667, 495 kDa. Lane 2: Loladder and Megaladder containing HA molecular mass markers 4570, 3050, 1520, 495, 310, 214, 110, and 30 kDa. Lane 3: ca. 2.5 µg HA eluted with 0.800 M NaCl solution after 0.360, 0.425 and 0.460 M NaCl stepwise elution. The HA amount is estimated from the ELSA data. Lane 4: The same sample as in Lane 3 after specific hyaluronidase digestion. The bands lower than 100 kDa are impurities and do not contain any HA.
Figure 8:
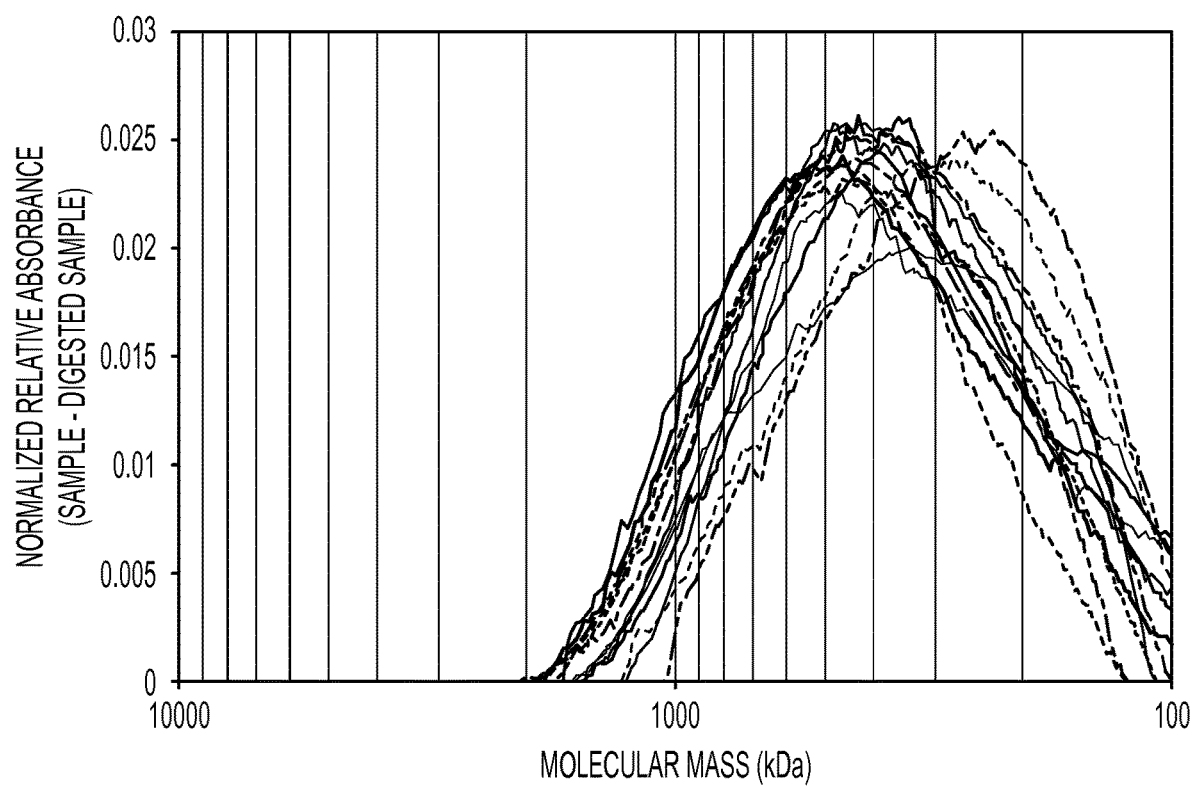
FIG. 8 is a densitometric analysis of electrophoretic separation of 0.800 M elutions of thirteen milk HA samples by IEX. The M distributions were obtained by subtracting the digested sample profiles from the corresponding undigested ones. The average M and range of M for each sample was obtained from these profiles. The M distributions are highly similar among thirteen independent milk samples.
Figure 12:
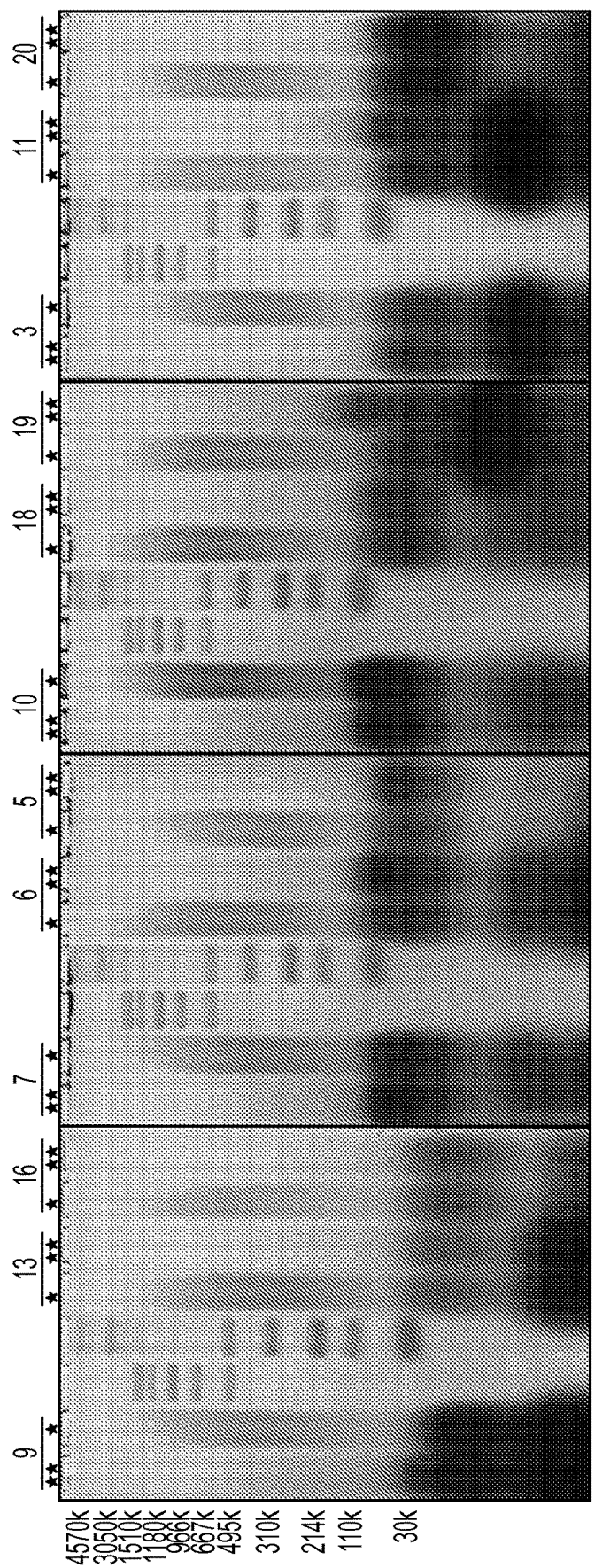
FIG. 12 shows the M distribution for the 0.800 M HA fraction from twelve human milk samples analyzed by 1% agarose gel electrophoresis. Star represents ~2.5 μg HA eluted with 0.800 M NaCl solutions after 0.360, 0.425 and 0.460 M NaCl elutions. The HA amount is estimated from the ELSA data. Double star represents the same corresponding sample after hyaluronidase digestion. The bands lower than 100 kDa are impurities and do not contain any HA. The M distributions were obtained by subtracting the bands of the digested sample from the corresponding undigested ones. The average M and range of M (width at half height) for each fraction has been obtained from these profiles, as described by Cowman et al. (2011) and Bhilocha et al. (2011). The gel results show that the M distributions are highly similar among twelve independent milk samples.

A more complete M distribution for the 0.800 M high M HA fraction from milk was separately determined by agarose gel electrophoresis. For the thirteen samples that had sufficient HA, the 0.800 M fraction of each sample was divided into two equal sets of ~2.5 μg HA (determined by ELSA) before loading onto a 1% agarose gel. One of the sets was predigested by an HA-specific hyaluronidase. A representative gel result is shown in FIG. 7. Comparison of lanes 3 and 4 indicates that no apparent impurity bands are overlapping with the main HA band (Note that the densitometric profiles in the region of the gel that would correspond to HA <100 kDa contains only contaminants, since all of the low M HA had been eluted from the IEX column at lower NaCl concentrations. Thus lane 4 shows that even after all purification steps, and digestion of all HA, a large amount of impurities, probably including unsulfated and undersulfated chondroitin, are still present in the sample). The molecular mass distributions for the milk HA samples eluted with 0.800 M NaCl were obtained by subtracting the densitometric profiles of the digested samples from the corresponding undigested ones. The average M and range of M for each sample was then obtained from these corrected profiles, as described by Cowman et al. (2011) and Bhilocha et al. (2011). High M HA was well separated on the 1% agarose gel. The M ranged from about 100-1500 kDa, with a weight-average M of 514 kDa for the sample shown in FIG. 7. The gel results for the twelve other milk 0.800 M fractions are presented in FIG. 12, and the densitometric profiles for all thirteen samples are shown in FIG. 8. Surprisingly, the plot shows that the M distributions were all highly similar among thirteen independent milk samples with initial HA concentrations ranging from 203 to 2736 ng/ml. The weight-average M of each sample is shown in Table 3. The average weight-average M of the thirteen samples was 440±60 kDa.

It was not possible to analyze the low M milk HA fractions by electrophoresis, as the sub-microgram amounts were too low to be detected properly by staining, and their migration positions in the gels would coincide with strongly staining impurities.

DISCUSSION

The combined use of IEX to fractionate HA on the basis of size, followed by quantification of HA in each fraction using a competitive ELSA assay yields a molecular mass distribution that is very similar to that obtained by established electrophoretic methods using pure HA. This demonstration is essential for application of the method to imperfectly purified HA isolated from limited biological sources. This method provides a novel and improved procedure, since it is not possible to analyze impure HA samples by electrophoretic analysis with nonspecific staining, and "Eastern" blotting with specific detection cannot detect HA less than 20 kDa and does not properly quantitate HA less than 150 kDa (Yuan et al., 2013).

The present investigation demonstrates the usefulness of ion exchange chromatography with ELSA in determining low molecular mass distribution of HA in human breast milk. The IEX fractionation can also be differentially optimized to provide HA fractions with specific average M by changing the salt concentrations of the eluting solutions. For example, the method can be used to separate fractions containing HA greater than about 80 kDa from various fractions containing low M HA of desired low polydispersity, in the range of about 7-80 kDa. This fractionation method for low M HA provides an improvement over existing SEC methods for separation and purification of HA according to M, by allowing batch-wise step elution for isolation of fractions of specified average M and low polydispersity in M. Analysis of the HA fractions by electrophoresis is not routinely necessary for analysis of biological HA samples, except for pre-determining the sizes of specific fractions.

Anion exchange chromatography with gradient elution using salt solutions of increasing ionic strength has been used previously to separate short oligosaccharide fragments of HA by degree of polymerization and thus total charge (since there is one negative charge per disaccharide repeat unit), but success has been limited to fragments containing from 1 to about 20 disaccharides (0.4-8 kDa) (Mahoney et al., 2001; Weissmann et al., 1954; Nebinger, 1985; Holmbeck et al., 1993; and Tawada et al., 2002). Short fragments of sulfated glycosaminoglycans, their desulfated products, or hybrid oligosaccharides created by transglycosylation have also been separated by anion exchange chromatography. Fragments containing 1 to approximately 20 disaccharides (ca. 10 kDa) were separated by size using an elution gradient of increasing ionic strength (Hoffman et al., 1956; Yamashina et al., 1963; Inoue et al., 1981; and Lauder et al., 2000). No glycosaminoglycans have previously been fractionated by size/degree of polymerization/total charge for sizes above about 8-10 kDa. It has generally been expected that fragments larger than about 10 kDa would not be fractionated on the basis of size using ion exchange methods, due to small differences in total charge between long chains. The results in this study show that this IEX separation technique is also able to fractionate HA fairly well into narrow sub-fractions up to around 100 kDa. M-dependent separation of HA above this size by IEX has been less successful.

Surface detection techniques for HA such as blotting or sandwich ELSAs have proven to be incapable of detecting HA below 20 kDa, and the signal for low M HA is significantly M-dependent (Yuan et al., 2013). A detection method that is able to "see" all sizes of HA equally is preferred. HA detection by a competitive ELSA assay is not sensitive to molecular mass as low as 6 kDa (Haserodt et al., 2011), because the HA-protein binding event occurs in solution phase. Thus, HA size fractionation with subsequent competitive ELSA assay is a suitable method for determination of HA molecular mass distribution. The sensitivity of the ELSA kit used in this study generally needs at least 20 ng per sample. The sensitivity could be further improved by using fluorescently labeled HA binding molecules (Martins et al., 2003). Where low M HA is a small fraction of the total HA present in a tissue or fluid, and the available quantity of HA may be small, the high sensitivity in detection afforded by an ELSA assay provides the necessary sensitivity.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adam N., P. Ghosh, Hyaluronan molecular weight and polydispersity in some commercial intra-articular injectable preparations and in synovial fluid, *Inflamm. Res.* 50: 294-299 (2001).

Armstrong S. E., D. R. Bell, Measurement of high-molecular-weight hyaluronan in solid tissue using agarose gel electrophoresis, *Anal. Biochem.* 308:255-264 (2002).

Baba, Y., C. Sumita, K. Hide, N. Ishimaru, K. Samata, A. Tanaka and M. Tsuhako, Separation of DNA fragments by high-performance liquid-chromatography and capillary electrophoresis, *Journal of Liquid Chromatography* 16: 955-965 (1993).

Baggenstoss B. A., P. H. Weigel, Size exclusion chromatography-multiangle laser light scattering analysis of hyaluronan size distributions made by membrane-bound hyaluronan synthase, *Anal. Biochem.,* 352:243-251 (2006).

Balazs E. A., Viscoelastic Properties of Hyaluronic Acid and biological lubrication, Univ. Mich. *Med. Cent. J.,* 255-259 (1968).

Ballard O., A. L. Morrow, Human milk composition: nutrients and bioactive factors, *Pediatr. Clin. North Am.* 60:49-74 (2013).

Bhilocha S., R. Amin, M. Pandya, H. Yuan, M. Tank, J. LoBello, A. Shytuhina, W. Wang, H. Wisniewski, C. A. de la Motte, M. K. Cowman, Agarose and polyacrylamide gel electrophoresis methods for molecular mass analysis of 5- to 500-kDa hyaluronan, *Anal. Biochem.* 417:41-49 (2011).

Bode L., Human milk oligosaccharides: every baby needs a sugar mama, *Glycobiology,* 22:1147-1162 (2012).

Coppa G. V., O. Gabrielli, P. Buzzega, L. Zampini, T. Galeazzi, F. Maccari, E. Bertino, N. Volpi, Composition and structure elucidation of human milk glycosaminoglycans, *Glycobiology* 21:295-303 (2011).

Cowman M K, Chen C C, Pandya M, Yuan H, Ramkishun D, LoBello J, Bhilocha S, Russell-Puleri S, Skendaj E, Mijovic J, Jing W. Improved agarose gel electrophoresis method and molecular mass calculation for high molecular mass hyaluronan. *Anal. Biochem.* 417:50-56 (2011).

Dahl L. B., I. M. Dahl, A. Engstrom-Laurent, K. Granath, Concentration and molecular weight of sodium hyaluronate in synovial fluid from patients with rheumatoid arthritis and other arthropathies, *Ann. Rheum. Dis.* 44:817-822 (1985).

Dahl L. B., I. M. Dahl, A. L. Borresen, The molecular weight of sodium hyaluronate in amniotic fluid, *Biochem. Med. Metab. Biol.* 35:219-226 (1986).

Haserodt S., M. Aytekin, R. A. Dweik, A comparison of the sensitivity, specificity and molecular weight accuracy the three different commercially available hyaluronan ELISA-like assays, *Glycobiology,* 21:175-183 (2011).

Hayase S., Y. Oda, S. Honda, K. Kakehi, High-performance capillary electrophoresis of hyaluronic acid: determination of its amount and molecular mass, *J. of Chrom. A.* 768: 295-305 (1997).

Hill D. R., H. K. Rho, S. P. Kessler, R. Amin, C. R. Homer, C. McDonald, M. K. Cowman, C. A. De La Motte, Human Milk Hyaluronan Enhances Innate Defense Of The Intestinal Epithelium, *J. Biol. Chem.,* 288:29090-29104 (2013).

Hill D. R., S. P. Kessler, H. K. Rho, M. K. Cowman, C. A. de la Motte, Specific-sized hyaluronan fragments promote expression of human β-defensin 2 in intestinal epithelium, *J. Biol. Chem.,* 287:30610-30624 (2012).

Hoffman P., K. Meyer, A. Linker, Transglycosylation during the mixed digestion of hyaluronic acid and chondroitin sulfate by testicular hyaluronidase, *J. Biol. Chem.* 219, 653-663 (1956).

Holmbeck, S. and L. Lerner, Separation of hyaluronan oligosaccharides by the use of anion-exchange HPLC., *Carbohydr Res,* 239: 239-244 (1993).

Holmes M. W., M. T. Bayliss, H. Muir, Hyaluronic acid in human articular cartilage. Age-related changes in content and size, *Biochem. J.,* 250: 435-441 (1988).

Inoue, Y. and K. Nagasawa, Depolymerization of glycosaminoglycuronans into di- and higher molecular-weight oligo-saccharides: improved preparation of N-acetyldermosine and oligomeric N-acetylchondrosines, *Carbohydr Res,* 97(2): 263-278 (1981).

Itano N., T. Sawai, M. Yoshida, P. Lenas, Y. Yamada, M. Imagawa, T. Shinomura, M. Hamaguchi, Y. Yoshida, Y. Ohnuki, S. Miyauchi, A. P. Spicer, J. A. McDonald, K. Kimata, Three isoforms of mammalian hyaluronan synthases have distinct enzymatic properties, *J. Biol. Chem.,* 274: 25085-25092 (1999).

Kato, Y., K. Nakamura and T. Hashimoto, "New ion exchanger for the separation of proteins and nucleic acids." *J Chromatogr* 266: 385-394 (1983).

Kato, Y., T. Kitamura, A. Mitsui, Y. Yamasaki, T. Hashimoto, T. Murotsu, S. Fukushige and K. Matsubara, Separation of oligonucleotides by high-performance ion-exchange chromatography on a non-porous ion exchanger., *J Chromatogr,* 447(1): 212-220 (1988).

Kato, Y., Y. Yamasaki, A. Onaka, T. Kitamura, T. Hashimoto, T. Murotsu, S. Fukushige and K. Matsubara, Separation of DNA restriction fragments by high-performance ion-exchange chromatography on a non-porous ion exchanger, *J Chromatogr,* 478: 264-268 (1989).

Kvam C., D. Granese, A. Flaibani, F. Zanetti, S. Paoletti, Purification and characterization of hyaluronan from synovial fluid, *Anal. Biochem.,* 211; 9-44 (1993).

Lauder, R. M., T. N. Huckerby and I. A. Nieduszynski, A fingerprinting method for chondroitin/dermatan sulfate and hyaluronan oligosaccharides, *Glycobiology* 10:393-401 (2000).

Laurent U. B. G., K. A. Granath, The molecular weight of hyaluronate in the aqueous humour and vitreous body of rabbit and cattle eyes, *Exp. Eye Res.,* 36:481-491 (1983).

Lee, H. G. and Cowman, M. K., An Agarose Gel Electrophoretic Method for Analysis of Hyaluronan Molecular Weight Distribution, *Anal. Biochem.*, 219: 278-287 (1994).

Mahoney D. J., R. T. Aplin, A. Calabro, V. C. Hascall, A. J. Day, Novel methods for the preparation and characterization of hyaluronan oligosaccharides of defined length, *Glycobiology*, 11:1025-1033 (2001).

Malm L., U. Hellman, G. Larsson, Size determination of hyaluronan using a gas-phase electrophoretic mobility molecular analysis, *Glycobiology*, 22:7-11 (2012).

Martins J. R. M., C. C. Passerotti, R. M. B. Maciel, L. O. Sampaio, C. P. Deitrich, H. B. Nader, Practical determination of hyaluronan by a new noncompetitive fluorescence-based assay on serum of normal and cirrhotic patients, *Anal. Biochem.*, 319:65-72 (2003).

Meran S., D. D. Luo, R. Simpson, J. Martin, A. Wells, R. Steadman, A. O. Phillips, Hyaluronan facilitates transforming growth factor-$\beta$1-dependent proliferation via CD44 and epidermal growth factor receptor interaction, *J. Biol. Chem.*, 286:17618-17630 (2011).

Min H, Cowman M K., Combined Alcian blue and silver staining of glycosaminoglycans in polyacrylamide gels: application to electrophoretic analysis of molecular weight distribution. *Anal. Biochem.*, 155:275-285 (1986).

Nebinger P., Comparison of gel permeation and ion-exchange chromatographic procedures for the separation of hyaluronate oligosaccharides, *J. Chromatogr.*, 320:351-359 (1985).

Newburg D. S., G. M. Ruiz-Palacios, A. L. Morrow, Human milk glycans protect infants against enteric pathogens, *Annu. Rev. Nutr.* 25: 37-58 (2005).

Newburg D. S., R. J. Linhardt, S. A. Ampofos, R. H. Yolken, Human Milk Glycosaminoglycans Inhibit HIV Glycoprotein gp120 Binding to Its Host Cell CD4 Receptor, *J. Nutr.*, 125:419-424 (1995).

Puré E., R. K. Assoian, Rheostatic signaling by CD44 and hyaluronan, *Cell Signal*, 21:651-655 (2009).

Ruscheinsky M., C. A. De la Motte, M. Mahendroo, Hyaluronan and its binding proteins during cervical ripening and parturition: dynamic changes in size, distribution and temporal sequence, *Matrix Biol.*, 27:487-497 (2008).

Sasaki Y., M. Uzuki, K. Nohmi, H. Kitagawa, A. Kamataki, M. Komagamine, K. Murakami, T. Sawai, Quantitative measurement of serum hyaluronic acid molecular weight in rheumatoid arthritis patients and the role of hyaluronidase, *Int. J. Rheum. Dis.*, 14:313-319 (2011).

Spicer A. P., J. Y. Tien, Hyaluronan and morphogenesis, *Birth Defects, Res C Embryo Today*, 72:89-108 (2004).

Strege, M. A. and A. L. Lagu, Anion-exchange chromatography of DNA restriction fragments, *J Chromatogr*, 555: 109-124 (1991).

Swann D. A., Studies on hyaluronic acid. I. The preparation and properties of rooster comb hyaluronic acid, *Biochim Biophys Acta*, 156:17-30 (1968).

Tammi R., U. M. Agren, A. L. Tuhkanen, M. Tammi, Hyaluronan metabolism in skin, *Prog. Histochem. Cytochem.*, 29:1-81 (1994).

Tawada A., T. Masa, Y. Oonuki, A. Watanabe, Y. Matsuzaki, A. Asari, Large-scale preparation, purification, and characterization of hyaluronan oligosaccharides from 4-mers to 52-mers, *Glycobiology*, 12:421-426 (2002).

Tengblad A., U. B. G. Laurent, K. Lilja, R. N. P. Cahill, A. Engstrom-Laurent, J. R. E. Fraser, H. E. Hansson, T. C. Laurent, Concentration and relative molecular mass of hyaluronate in lymph and blood, *Biochem. J.*, 236:521-525 (1986).

Tolg C., S. R. Hamilton, E. Zalinska, L. McCulloch, R. Amin, N. Akentieva, F. Winnik, R. Savani, D. J. Bagli, L. G. Luyt, M. K. Cowman, J. B. McCarthy, E. A. Turley, A RHAMM mimetic peptide blocks hyaluronan signaling and reduces inflammation and fibrogenesis in excisional skin wounds, *Am. J. Pathol.*, 181:1250-1270 (2012).

Turner R. E., P. Y. Lin, M. K. Cowman, Self-association of hyaluronate segments in aqueous NaCl solution, *Arch. Biochem. Biophys*, 265: 484-495 (1988).

Volpi N., On-Line HPLC/ESI-MS Separation and Characterization of Hyaluronan Oligosaccharides from 2-mers to 40-mers, *Anal. Chem.*, 79:6390-6397 (2007).

Weissmann, B., K. Meyer, P. Sampson and A. Linker, Isolation of oligosaccharides enzymatically produced from hyaluronic acid, *J Biol Chem*, 208:417-429 (1954).

Yamashina, I., M. Makino, Y. Miyakoshi and K. Sakai, Chromatographic separation of sulfated oligosaccharides, *Biochim Biophys Acta* 74:295-297 (1963).

Yeung B., D. Marecak, Molecular weight determination of hyaluronic acid by gel filtration chromatography coupled to matrix-assisted laser desorption ionization mass spectrometry, *J. of Chrom. A.*, 852: 573-581 (1999).

Yuan, H., Tank, M., Alsofyani, A., Shah, N., Talati, N., LoBello, J. C., Kim, J. R., Oonuki, Y., de la Motte, C. A., and Cowman, M. K., Molecular mass dependence of hyaluronan detection by sandwich ELISA-like assay and membrane blotting using biotinylated HA binding protein, *Glycobiology* 23:1270-1280 (2013).

What is claimed is:

1. A method for separating hyaluronan (HA) on the basis of molecular mass (M), comprising:
    applying a sample of HA to an anion exchange matrix;
    eluting the HA in the sample with salt solutions or a salt solution gradient of increasing concentration into a plurality of fractions to separate HA by size, wherein HA present in the sample in a size range between 20 to 150 kDa are separated into at least three different size range fractions.

2. The method of claim 1, wherein the specific size range in each size range fraction is determined by correlation of HA size reference standards with salt concentration for elution from the anion exchange matrix.

3. The method of claim 1, wherein HA in the sample in a size range of 20 to 80 kDa are separated into at least three different size range fractions.

4. The method of claim 1, wherein HA in the sample is separated into at least three different size range fractions, at least two of which are in the size range of 20 to 80 kDa.

5. The method of claim 4, wherein HA greater than 80 kDa is separated into at least one size fraction.

6. The method of claim 1, wherein HA in the sample is separated into at least three different size range fractions, at least two of which are in the size range of 20 to 100 kDa.

7. The method of claim 4, wherein HA greater than 100 kDa is separated into at least one size fraction.

8. The method of claim 1, wherein HA in the sample is separated into at least four different size range fractions, at least three of which are in the size range of 20 to 110 kDa.

9. The method of claim 8, wherein HA greater than 110 kDa is separated into at least one size fraction.

10. The method of claim 1, further comprising isolating a size fraction of HA from among the different size fractions.

11. The method of claim 10, wherein the isolating step comprises further purification of the HA in the isolated size fraction.

12. An assay for quantifying in a sample the amount of HA in a size range of about 20 to 150 kDa, comprising:
   applying the method of claim 1 to fractionate HA in a sample by size; and
   determining the amount of HA in the sample in each of the plurality of size range fractions.

13. The assay of claim 12, wherein the determining step is performed with enzyme-linked immunosorbent (ELISA)-like assay using an HA binding molecule.

14. The assay of claim 13, wherein the ELISA-like assay is an enzyme-linked sorbent assay.

15. The assay of claim 13, wherein the HA binding molecule is selected from the group consisting of aggrecan proteoglycan, the HA binding region (HABR) of aggrecan proteoglycan, versican proteoglycan, an HA-binding portion of versican proteoglycan, hyaluronectin, and any mixture thereof.

16. The assay of claim 14, wherein the HA binding molecule is selected from the group consisting of aggrecan proteoglycan, the HA binding region (HABR) of aggrecan proteoglycan, versican proteoglycan, an HA-binding portion of versican proteoglycan, hyaluronectin, and any mixture thereof.

17. The method of claim 1, wherein the sample from which HA is separated by size is a human milk sample.

\* \* \* \* \*